(12) United States Patent
Cao et al.

(10) Patent No.: US 6,284,464 B1
(45) Date of Patent: Sep. 4, 2001

(54) INHIBITION OF BINDING OF HOX AND HOMEODOMAIN-CONTAINING PROTEINS AND USES THEREOF

(75) Inventors: Xu Cao; Xingming Shi; Xiangli Yang, all of Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/286,682

(22) Filed: Apr. 5, 1999

Related U.S. Application Data

(60) Provisional application No. 60/080,859, filed on Apr. 6, 1998, now abandoned.

(51) Int. Cl.[7] .............................. C12Q 1/68; C12N 15/63
(52) U.S. Cl. ................... 435/6; 435/7.8; 435/455
(58) Field of Search ................... 435/355, 69.1, 435/365, 372, 6, 7.8, 7.1, 455; 514/2, 44

(56) References Cited

U.S. PATENT DOCUMENTS 5,693,615 * 12/1997 Stone ....................... 514/12

OTHER PUBLICATIONS

Langer, Drug Delivery and Targeting, Nature 392, suppl. p 5–10, Apr. 30, 1998.*

Anderson, Human Gene Therapy, Nature 392, suppl. p25–30, Apr. 30, 1998.*

* cited by examiner

*Primary Examiner*—Robert A. Schwartzman
(74) *Attorney, Agent, or Firm*—Benjamin Aaron Adler

(57) ABSTRACT

The present invention demonstrates that BMP-2/4 activates osteopontin gene transcription by removing Hoxc-8 binding through Smad1 interaction with the Hoxc-8 DNA binding domain. Since the DNA binding domain is conserved in all Hox and homeodomain-containing proteins, Smad1 likely interacts with all Hox or homeodomain-containing proteins. Furthermore, the present invention reveals the Smad1-mediated transcriptional mechanism in the BMP-2/4 signaling pathway and also provides information about the transcriptional roles of the Hox genes during embryonic development.

6 Claims, 22 Drawing Sheets

SEQUENCE LISTING

<160> NUMBER OF SEQ ID NOS: 11

<210> SEQ ID NO 1
<211> LENGTH: 15
<212> TYPE: DNA
<213> ORGANISM: artificial sequence -continued

```
<220> FEATURE:
<223> OTHER INFORMATION: Forward strand of oligonucleotide Probe S

<400> SEQUENCE: 1
agggtaattg gaggc                                                    15

<210> SEQ ID NO 2
<211> LENGTH: 15
<212> TYPE: DNA
<213> ORGANISM: artificial sequence
<220> FEATURE:
<223> OTHER INFORMATION: Reverse strand of oligonucleotide Probe S

<400> SEQUENCE: 2
gcctccaatt accct                                                    15

<210> SEQ ID NO 3
<211> LENGTH: 26
<212> TYPE: DNA
<213> ORGANISM: artificial sequence
<220> FEATURE:
<223> OTHER INFORMATION: Forward strand of oligomer OPN-4

<400> SEQUENCE: 3
catgacccca attagtcctg gcagca                                        26

<210> SEQ ID NO 4
<211> LENGTH: 20
<212> TYPE: DNA
<213> ORGANISM: artificial sequence
<220> FEATURE:
<223> OTHER INFORMATION: Reverse strand of oligomer OPN-4

<400> SEQUENCE: 4
cagggatcca taaggaaagg                                               20

<210> SEQ ID NO 5
<211> LENGTH: 24
<212> TYPE: DNA
<213> ORGANISM: artificial sequence
<220> FEATURE:
<223> OTHER INFORMATION: Forward strand of oligomer OPN-5

<400> SEQUENCE: 5
gacatcgttc atcagtaatg cttg                                          24

<210> SEQ ID NO 6
<211> LENGTH: 24
<212> TYPE: DNA
<213> ORGANISM: artificial sequence
<220> FEATURE:
<223> OTHER INFORMATION: Reverse strand of oligomer OPN-5

<400> SEQUENCE: 6
caagcattac tgatgaacga tgtc                                          24

<210> SEQ ID NO 7
<211> LENGTH: 25
<212> TYPE: DNA
<213> ORGANISM: artificial sequence
<220> FEATURE:
<223> OTHER INFORMATION: Forward strand of oligomer OPN-6

<400> SEQUENCE: 7
gacatcgttc atcagtaatg ctttg                                         25
```

```
<210> SEQ ID NO 8
<211> LENGTH: 25
<212> TYPE: DNA
<213> ORGANISM: artificial sequence
<220> FEATURE:
<223> OTHER INFORMATION: Reverse strand of oligomer OPN-6

<400> SEQUENCE: 8
caaagcatta ctgatgaacc atgtc                                 25

<210> SEQ ID NO 9
<211> LENGTH: 25
<212> TYPE: DNA
<213> ORGANISM: artificial sequence
<220> FEATURE:
<223> OTHER INFORMATION: Osteopontin Hoxc-8 binding site

<400> SEQUENCE: 9
ggtagttaat gacatcgttc atcag                                 25

<210> SEQ ID NO 10
<211> LENGTH: 25
<212> TYPE: DNA
<213> ORGANISM: artificial sequence
<220> FEATURE:
<223> OTHER INFORMATION: Mutated osteopontin Hoxc-8 binding site

<400> SEQUENCE: 10
ggtagtgccg gacatcgttc atcag                                 25

<210> SEQ ID NO 11
<211> LENGTH: 6
<212> TYPE: PRT
<213> ORGANISM: artificial sequence
<220> FEATURE:
<221> NAME/KEY: DOMAIN
<222> LOCATION: 137..142
<223> OTHER INFORMATION: hexapeptide upstream from the homeodomain in
      Hoxc-8

<400> SEQUENCE: 11

Leu Met Phe Pro Trp Met
1               5
```

INHIBITION OF BINDING OF HOX AND HOMEODOMAIN-CONTAINING PROTEINS AND USES THEREOF

CROSS-REFERENCE TO RELATED APPLICATION

This patent application claims benefit of provisional patent application U.S. Ser. No. 60/080,859, filed Apr. 6, 1998, now abandoned.

FEDERAL FUNDING LEGEND

This invention was produced in part using funds obtained through grant DK53757 from the National Institute of Health. Consequently, the federal government has certain rights in this invention.

BACKGROUND OF THE INVENTION

1. Field of the Invention

The present invention relates generally to the fields of transcriptional regulation. More specifically, the present invention relates to inhibition of binding of hox and homeodomain-containing proteins and uses thereof.

2. Description of the Related Art

The bone morphogenetic proteins (BMPs), a subfamily of TGFβ, are potent growth factors that regulate embryonic development, vertebral patterning and mesenchymal cell differentiation (1, 2). BMP-2/4, identified as bone inductive growth factors, are important signaling molecules during development of the skeleton in vertebrates (1, 3, 4). Central to the bone morphogenetic protein signaling pathway is the Smad1 protein, which translocates into the nucleus to regulate gene transcription upon direct phosphorylation by bone morphogenetic protein receptors (5–7).

Growth factors in the TGFβ superfamily have been implicated in various processes during vertebrate embryonic development. The TGFβ action on induction and patterning of mesoderm and skeletal development has been studied intensely. In particular, the TGFβ related molecules, BMP-2/4 induces skeletal patterning, growth of limb buds and skeletal cell differentiation. Hox and homeodomain containing transcription factors are also involved in the same process, and have been suggested as a downstream regulation of BMP-4 to mediate its effects. However, there has been little progress in understanding how hox proteins function in embryonic development. Although hox proteins are DNA binding proteins, very little is known about their natural DNA response elements and their role in transcription.

In vertebrates, there are 39 Hox homeobox-containing transcription factor genes, organized into four separate chromosome clusters, which play critical roles in the process and patterning of vertebrate embryonic development (8,18). These 39 genes are subdivided into 13 paralogous groups on the basis of duplication of an ancestral homeobox cluster during evolution, sequence similarity and position within the cluster (9). Each paralog group has been demonstrated to be responsible for morphogenesis of a particular embryonic domain or structure (8). There are three members in Hox paralog group VIII, Hoxb-8, Hoxc-8 and Hoxd-8 (9). Hox genes are required during vertebrate limb bud development, and particularly, Hoxb-8 was suggested to be a transcription factor involved in activating the Sonic hedgehog gene, which is the key mediator in limb development (10,11). Furthermore, Northern blot analysis shows that Hoxc-8 is expressed during human embryo development at high levels in spinal cord, backbone and limbs and at a lower level in heart (12). BMP-2/4 activates expression of Hox genes, induces osteoblast differentiation and controls patterning across the anteroposterior (a-p) axis of developing limb (13).

The prior art is deficient in methods for stimulating osteoblast differentiation and bone formation. The prior art is also deficient in methods of regulating transcription via the Hox proteins and/or homeobox-containing proteins. The present invention fulfills this long-standing need and desire in the art.

SUMMARY OF THE INVENTION

The bone morphogenetic protein-2 (BMP-2) was identified as a bone inductive growth factor, involved in inducing osteoblast differentiation. Central to the bone morphogenetic protein signaling pathway is the Smad1 protein, which translocates into the nucleus to activate osteoblast-specific gene transcription upon direct phosphorylation by bone morphogenetic protein receptors. The present invention identifies a specific interaction of Smad1 with Hox and homeodomain-containing proteins, which often act as transcriptional repressors, in which the binding of Smad1 to Hoxc-8 inhibits the recognition and binding of Hoxc-8 to its DNA binding site in a dose-dependent manner. This specific interaction between Smad1 and Hoxc-8 can be used as a target to inhibit the binding of Hoxc-8 to its DNA binding sites, thereby inducing osteoblast differentiation and preventing osteoporosis. The interaction of Smad1 with other Hox proteins or homeobox-containing proteins may also be used to regulate other diseases, such as cancer or cardiovascular disease.

In an embodiment of the present invention, there is provided a method of stimulating bone formation in an individual, comprising the step of: inducing an interaction between Smad1 and a homeobox-containing transcription factor. Preferably, this interaction induces a BMP-responsive gene which encodes a bone matrix protein. This induction results in osteoblast and/or chondroblast differentiation, which in turn, stimulates bone formation.

In another embodiment of the present invention, there is provided a method of inducing gene(s) encoding bone matrix proteins, comprising the step of: inducing an interaction between Smad1 and a homeobox-containing transcription factor in which the interaction results in an induction of gene(s) encoding bone matrix proteins. Specifically, there is provided a method of inducing a gene encoding osteopontin, comprising the steps of: inducing an interaction between Smad1 and Hoxc-8. Preferably, this interaction results in removal of the transcriptional repression and induction of the gene encoding osteopontin.

In still yet another embodiment of the present invention, there is provided a method of screening for a compound that stimulates bone formation, comprising the steps of: contacting a cell with a compound; and determining the ability of the compound to inhibit binding of Hoxc-8 to a gene. This inhibition of binding results in induction of the gene which indicates that the compound stimulates bone formation.

In yet another embodiment of the present invention, there is provided a method of regulating disease in an individual, comprising the step of: inhibiting the binding of a homeobox-containing transcription factor to a gene involved in regulating disease, wherein the inhibition removes transcriptional repression of the gene by the homeobox-containing protein and results in the induction of those genes involved in regulating disease.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows the two-hybrid growth assay of interaction between Smad1 and Hoxc-8. Specific interactions were noted in yeast bearing both pGBT9-Smad1 and PAC-Hoxc-8 plasmids, which grew on media lacking His, Leu and Trp. FIG. 1B shows the β-gal liquid assay for two-hybrid assays. β-galactosidase activities for yeast bearing plasmids as indicated were plotted/Hoxc-8 in a pulldown. Hoxc-8 protein was labeled with FIG. 2 shows the interaction of Smad1 with Hoxc-8 inhibits Hoxc-8 function as a repressor.

FIG. 3A shows the DNA probes of osteopontin promoter that were used for EMSA in FIG. 3B, 3C, 3D, 3E, 3F and 3G. FIG. 3B shows that the OPN-2 DNA fragment contains a Hoxc-8 binding site. EMSA was performed using different $^{32}$P-labeled DNA fragments: OPN-1 (lanes 1–3), OPN-2 (lanes 4–6) and OPN-3 (lanes 7–9), and incubated with probe alone (lanes 1, 4 and 7), GST (lanes 2, 5, and 8) or GST-Hoxc-8 (lanes 3, 6 and 9). FIG. 3C shows that OPN-5 is the Hoxc-8 binding site. EMSA was performed using smaller $^{32}$P-labeled DNA fragments: OPN-4 (lanes 1–5), OPN-5 (lanes 6–10) and OPN-6 (lanes 11–15), and incubated with probe alone (lanes 1, 6 and 11), GST(lanes 2, 7, and 12), GST-Smad1 (lanes 3, 5, 8, 10, 13 and 15) or GST-Hoxc-8 (lanes 4,5, 9, 10, 14, and 15). FIG. 3D shows that Hoxc-8 specifically binds to OPN-5. EMSA was performed using $^{32}$P-labeled OPN-5 alone (lane 1) or with GST-Hoxc-8 (lanes 2–8). Lanes 3–5 and 6–8 contained 5-, 25-, and 100-fold molar excess of unlabeled OPN-5 and MSX-2 DNA binding element (Probe-M). FIG. 3E shows that Smad1 inhibits binding of Hoxc-8 to OPN-5 in a concentration-dependent manner. EMSA was performed using $^{32}$P-labeled OPN-5 alone (lane 1), with 1.5 μg GST (lane 2), 1.5 μg GST-Smad1 (lane 3) or 0.2 μg GST-Hoxc-8 protein (lanes 4–7) and different amounts of GST-Smad1 (1.5, 3 and 4.5 μg for lanes 5–7, respectively). FIG. 3F shows that Hox proteins interact with Smad1 and -4 but not Smad2 and -3. Hoxa-9 and Hoxc-8 GST fusion proteins (0.2 μg) were tested for their ability to interact with Smad1, -2, -3 and -4 or GST (3 μg) in a gel shift assay. FIG. 3G shows that Smads do not inhibit binding of Msx-1 and Msx-2 homeodomains containing proteins to their cognate DNA element. Purified GST-Msx-1 or -Msx-2 (0.5 μg) was incubated together with probe-M and different Smads (3 μg).

FIG. 4A shows a schematic description of the constructs used in the transfection assays: OPN-266 is the native osteopontin construct; Hox-pGL3 contains the osteopontin Hox binding site (Seq ID NO:9) linked to the SV40 promoter; mHOX-pGL3 contains the mutated osteopontin Hox binding site (Seq ID NO:10). FIG. 4B shows that BMP activates the osteopontin promoter. The OPN-266 plasmid was co-transfected in C3H10T1/2 mesenchymal cells with Hoxc-8, Smad1, or Smad4 plasmids alone or in a combination of all three in the presence or absence of ALK3 plasmid. FIG. 4C shows the osteopontin Hox binding site mediates BMP-induced transcription. Hox-pGL3 construct was co-transfected with ALK6 or ALK3 in C3H10T1/2 mesenchymal cells. FIG. 4D shows that mutation of Hox binding site abolishes BMP stimulation. Hox-pGL3 construct or mHox-pGL3 control plasmid was co-transfected with ALK6, ALK3 or Hoxc-8 plasmids in C3H10T1/2 mesenchymal cells. Cell lysates were assayed for luciferase activity normalized to Renilla luciferase levels 48 h after transfection. Experiments were repeated twice in triplicate.

FIG. 5A shows a SDS-PAGE profile of purified GST-Smad1 fragments used in the gel shift assays shown in panel B and schematic presentation of Smad1 deletion constructs. Bacterial expressed GST recombinant Smad1 proteins as indicated in amino acid numbers were purified on glutathione-agarose. Glutathione elutions were loaded onto a 10% SDS-PAGE and visualized by Coomassie Blue staining (left panel). The sizes of each were verified with the molecular mass markers on the top lane of the gel. FIG. 5B shows that two regions of Smad1 confer the inhibitory effect on Hoxc-8 binding. Gel shift assay was performed using purified GST fusion proteins and [$^{32}$P]-labeled probe derived from osteopontin promoter ~206 to ~180. Lane 1, probe alone, lanes 2–16, probe with GST (lane 2), or with GST-Hoxc-8 in the absence (lane 4) or presence of various sized Smad1 proteins (lanes 5–16). Two regions (aa 101–145 in MH1 and 148–191 in MH1-linker junction) were mapped to be sufficient for the interaction (lanes 14 and 16). FIG. 5C shows that inhibition by Smad1 fragments of Hoxc-8 binding to DNA is dose-dependent. Hoxc-8 was incubated with the same probe in the absence (lane 1) and the presence of Smad1 fragments 101–145 (lanes 2–4) or 148–191 (lanes 5–7) with a 2-fold increase in truncated Smad1 concentration between successive lanes.

FIG. 6A shows schematic illustrations of various deletion mutants of Hoxc-8 used for interaction studies. The size of each is labeled by the amino acid residues. CR1, conserved region 1; HP, hexapeptide; HDC, homeodomain and its C-terminal extension; and HD, homeodomain. FIG. 6B shows the interaction between Smad1 and Hoxc-8 in yeast two-hybrid system. Yeast strain Y190 containing the plasmid pGBT9/Smad1 was transformed with pACT2 (control) or pACT2 containing various-sized Hoxc-8 cDNA as indicated. Transformants (colonies) were assayed for the β-galactosidase activities and the values were normalized for the cell densities. Each bar represents the mean±SD from three independent determinations. FIG. 6C shows that the homeodomain and its C-terminal extension of Hoxc-8 are involved in the interaction with Smad1 MH1 domain. Bacterially expressed GST-HDC was incubated with the same probe used in FIG. 5 in the absence (lane 4) and presence (lanes 5–14) of various deletions of Smad1 as indicated on the top. Negative controls include probe alone (lane 1), with GST (lane 2), and with GST-Smad1 (lane 3). FIG. 6D shows that the homeodomain of Hoxc-8 interacts with various Smad1 derivatives. GST-HD was assayed for the binding activity in a similar gel shift assay as in panel C.

FIG. 7A shows the constructs of Smad1-NL, Smad1-L, and Smad1-M. pTet-Splice vector was used to make tetracyclin (Tet)-regulated mammalian expression plasmids for Smad1-NL (aa 3-276), -L (aa 145-276), and -M (aa 104-191). A nuclear localization signal (NLS) was fused to each construct allow the expressed truncated proteins to enter the nucleus. FIG. 7B shows that expression of Smad1 fragments is Tet regulated. Constructs shown in panel A were permanently transfected into 2T3 osteoblast precursor cells and the total RNA was extracted after 2-day culturing the cells in the absence or presence of Tet. The expression of each Smad1 fragment was induced upon Tet withdrawal. FIG. 7C shows that alkaline phosphatase activity is induced by the Hoxc-8 interaction domains of Smad1. 2T3 cells bearing pTet-Splice vector (vector), pTet-Splice/Smad1-NL (Smad1-NL), or Smad1-L was cultured in the presence or absence of Tet and the cells were lysed at indicated days (x-axis). Alkaline phosphatase activity was determined as described herein and the values were normalized for the protein contents. Each bar represents at least 3 independent measurements. FIG. 7D shows that Smad1 fragments induce mineral matrix formation in 2T3 clones. Indicated stable clones were cultured in the presence or absence of Tet or in the presence of 100 ng/ml BMP-2 (BMP-2) for 12 days. Cells then were fixed and stained by the von Kossa method. Mineral crystals (black spots) were formed in cells treated with BMP-2, and in the cell containing Hoxc-8 interaction domain of Smad1.

DETAILED DESCRIPTION OF THE INVENTION

Figure 1A:
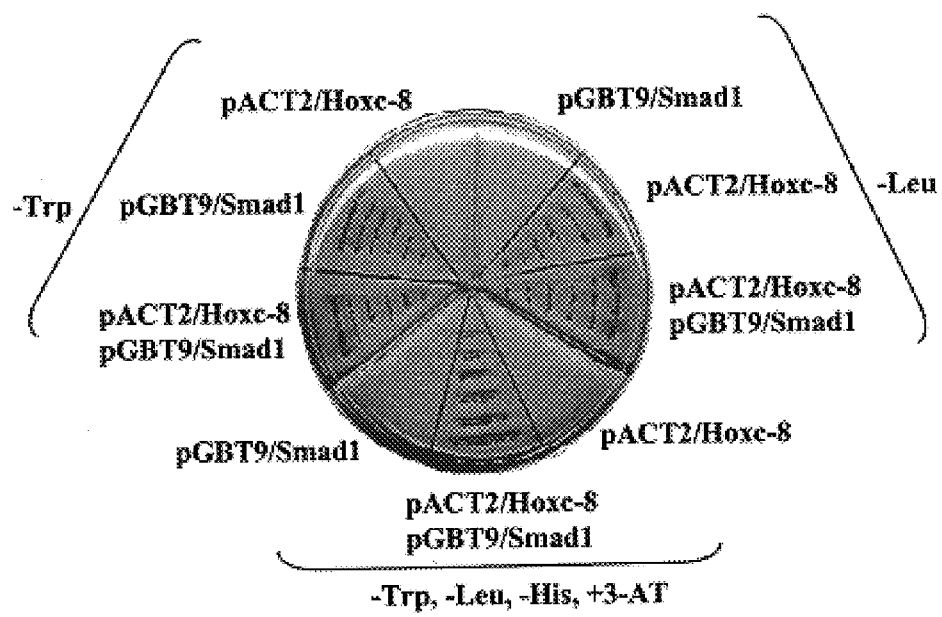
FIGS. 1A–1B show the specific interactions of Smad1 with Hoxc-8 in a two-hybrid system.

Signal transduction in the TGF-β superfamily requires the interaction of two types of serine/threonine transmembrane kinase receptors (5). The signaling is mediated by direct phosphorylation of Smad proteins. Phosphorylation of Smad2 and Smad3 is by TGFβ and activin (5,14), whereas Smad1 and SmadS are specifically induced by bone morphogenetic proteins, which are members of the TGF-β superfamily (6,7). Upon phosphorylation, the Smad proteins interact with a common partner, Smad4, and translocate into the nucleus where the complex recruits DNA binding protein (s) to activate specific gene transcription (6,14–17). However, the DNA binding protein(s) involved in bone morphogenetic protein signaling have not been identified.

This invention demonstrates that Smad1 specifically interacts with Hoxc-8, a member of the homeodomain transcription factor family, inhibiting binding of Hoxc-8 to its DNA binding site in a dose dependent manner. Hoxc-8 functions as a transcriptional repressor and is predominantly expressed in bone tissues. Furthermore, a Hoxc-8 binding site has been characterized from the 5'-flanking region of the osteopontin gene, whose expression is rapidly induced by BMP-2/4. It appears that bone morphogenetic protein-induced osteopontin gene transcription is mediated through the Hoxc-8 binding site.

The present invention is directed towards a method of stimulating bone formation in an individual, comprising the step of: inducing an interaction between Smad1 and a homeobox-containing transcription factor, wherein the interaction induces a BMP-responsive gene encoding a bone matrix protein which results in osteoblast and/or chondroblast differentiation, which subsequently stimulates bone formation. Representative means of inducing the interaction include phosphorylation of Smad1, overexpression of Smad1, and mutation of the homeobox-containing transcription factor. Generally, the homeobox-containing transcription factor is Hoxc-8, Hoxa-9, Msx-1, or Msx-2 and the BMP-responsive gene may include the genes encoding osteopontin, sialoprotein, osteonectin, or osteocalcin. Typically, the individual is osteopenic.

The present invention is also directed towards a method of inducing gene(s) encoding bone matrix proteins, comprising the step of: inducing an interaction between Smad1 and a homeobox-containing transcription factor in which the interaction results in an induction of gene(s) encoding bone matrix proteins. Representative means of induction are described above, as are representative homeobox-containing transcription factors and BMP-responsive genes. Specifically, the present invention is directed towards a method of inducing a gene encoding osteopontin, comprising the steps of: inducing an interaction between Smad1 and Hoxc-8, wherein the interaction results in removing transcriptional repression of a gene encoding osteopontin which induces the gene encoding osteopontin.

The present invention is still further directed towards a method of screening for a compound that stimulates bone formation, comprising the steps of: contacting a cell with a compound; and determining the ability of the compound to inhibit binding of Hoxc-8 to a gene. Inhibition of binding results in induction of the gene, which is indicative of a compound that stimulates bone formation. Representative compounds include an antibody or fragment thereof, synthetic drugs, synthetic proteins or a phosphorylated form of Smad1 or fragments thereof. Inhibition of binding can be determined by methods such as a gel-shift assay, transcription, Northern blotting, and Western blotting. As above, representative genes include the genes encoding osteopontin, sialoprotein, osteonectin, and osteocalcin.

The present invention is additionally directed towards a method of regulating disease in an individual, comprising the step of: inhibiting the binding of a homeobox-containing transcription factor to a gene involved in regulating disease in cells of the individual. Inhibition of binding removes transcriptional repression by the homeobox-containing protein, thereby resulting in the induction of the genes involved in regulating disease. In this case, inhibition may be due to the presence of a compound that binds to the homeobox-containing transcription factor, thereby inhibiting the DNA binding ability of the homeobox-containing transcription factor. As above, representative compounds include an antibody or fragment thereof, synthetic drugs, synthetic proteins and a phosphorylated form of Smad1 or fragments thereof. Preferred homeobox-containing transcription factors are Hoxc-8, Hoxa-9, Msx1, and Msx2. This method may be applied to individuals with osteoporosis, cancer, cardiovascular disease and neurological disease.

As used herein, the term "BMP-induced gene activation" shall refer to any genes that are induced to express upon the stimulation by BMPs.

As used herein, the term "Smad1" shall refer to any proteins that are homologous to Drosophila mothers against DPP or MAD protein.

As used herein, the phrase "interaction between Smad1 and Hox" or "interaction between Smad1 and a homeodomain-containing protein" shall refer to any interaction between the two proteins that results in a disruption of the transcription repressor activity of the Hox or homeodomain-containing proteins.

As used herein, the term "transcriptional repression by a hox protein" or "transcriptional repression by a homeodomain-containing protein shall refer to any gene whose transcription activities are repressed in the presence of the hox protein or the homeodomain-containing protein.

In accordance with the present invention, there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. DNA structures are discussed herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with a host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from a mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, repressors, polyadenylation signals, terminators, and the like, that provide for the expression of a coding sequence in a host cell. A "cis-element" or "DNA binding recognition sequence" is a nucleotide sequence, also termed a "consensus sequence" or "motif", that interacts with other proteins which can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the -10 and -35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method of use. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "orestriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene can be used to transform a host using any of the techniques commonly known to those of ordinary skill in the art. One preferred embodiment is the use of a vector containing coding sequences for a gene for purposes of prokaryotic transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous' region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, "fragment," as applied to a polypeptide or an antibody, will ordinarily be at least 10 residues, more typically at least 20 residues, and preferably at least 30 (e.g., 50) residues in length, but less than the entire, intact sequence. Fragments can be generated by methods known to those skilled in the art, e.g., by enzymatic digestion of naturally occurring or recombinant protein, by recombinant DNA techniques using an expression vector that encodes a defined fragment, or by chemical synthesis. The ability of a candidate fragment to exhibit a characteristic of Smad1 (e.g., binding to Hoxc-8) can be assessed by methods described herein. Purified fragments of Smad1 or antigenic fragments of Smad1 can be used to generate antibodies by employing standard protocols known to those skilled in the art.

A standard Northern blot assay can be used to ascertain the relative amounts of mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of a gene in transgenic systems, in accordance with conventional Southern hybridization techniques known to those of ordinary skill in the art. Both the Northern blot and Southern blot use a hybridization probe, e.g. radiolabelled cDNA, either containing the full-length, single stranded DNA or a fragment of that DNA sequence at least 20, preferably at least 30, more preferably at least 50, and most preferably at least 100 consecutive nucleotides in length. The DNA hybridization probe can be labelled by any of the many different methods known to those skilled in this art.

The labels most commonly employed for these studies are radioactive elements, enzymes, chemicals which fluorescent when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

The following examples are given for the purpose of illustrating various embodiments of the invention and are not meant to limit the present invention in any fashion:

EXAMPLE 1

Two-Hybrid Library Screening

The Smad1 cDNA was cloned into the SalI/PstI sites of pBGT9 vector to generate the pGBT9/Smad1 bait plasmid. Using the bait plasmid, human U2 OS osteoblast-like pACT cDNA library was screened following the procedure provided by the manufacturer (Clontech, Calif.). For confirmation of the interaction of Hoxc-8 with Smad1, a full length mouse Hoxc-8 cDNA was subcloned into the pACT vector at XhoI and EcoRI sites. The pACT/Hoxc-8 was cotransformed with pGBT9/Smad1 into Y190 and the colonies were assayed for β-galactosidase expression using both colony lift filter assay and liquid assay.

EXAMPLE 2

Expression and Purification of Glutathione S-Transferase (GST) Fusion Proteins

GST fusion constructs of GST-Smad1 and -Smad3 were generated by restriction digest of pGBT-Smad1 (SalI/HindIII) and pCMV5-Smad3 (BamHI/SalI) and subsequently inserted into the SalI/HindIII and BamHI/SalI sites of the PGEX-KG vector, respectively. GST-Smad2 and -Smad4 were digested with EcoRI/SalI from pCMV5-Smad2 and pCMV5-Smad4 and inserted into the EcoRI/SalI sites of the pGEX-5X-2 and pGEX-5X-1 vector (Amersham Pharmacia Biotech), respectively. The GST-Hoxc-8 and GST-Hoxa-9 were amplified by PCR using high fidelity Pfu-Turbo DNA polymerase (Stratagene) and cloned in the BamHI/EcoRI and BamHI/XbaI sites of the pGEX-KG vector, respectively. The GST-Msx-1 and -Msx-2 expression plasmids were provided by Dr. C. Abate-Shen (Center for Advanced Biotechnology and Medicine, Piscataway, N.J.). The GST constructs described above were transformed into BL21 and expression and purification of the fusion proteins were performed.

EXAMPLE 3

GST Pulldown Assay

Smad1 or Hoxc-8 was translated in the presence of $[^{35}S]$ methionine with linearized Smad1 or Hoxc-8 pBluescript (SK) plasmid, respectively, using the TNT-coupled reticulocyte lysate system according to the procedure by the manufacturer (Promega). The labeled Smad1 protein was confirmed by SDS-PAGE.

Smad1-containing lysate (5 μl) was mixed with an equivalent amount (1 μg) of GST alone or GST-Hoxc8. Alternatively, Hoxc-8-containing lysate was mixed with GST alone or GST-Smad1. The samples were incubated for 30 min on ice before GST-agarose diluted in NENT buffer (50 μl) was added to each sample and followed by a 30 min incubation at 4° C. The Sepharose beads were washed four times in a PBS/0.1% TritonX-100 solution, and bound proteins were eluted by incubation in 2×SDS-buffer for 5 min at 10° C. The labeled Smad1 protein in vitro translated lysate (1 μg) was loaded as input together with the eluted samples on a 12.5% SDS-PAGE.

EXAMPLE 4

Immunoprecipitation and Western Blot

HA-tagged Hoxc-8 was subcloned from pACT2/Hoxc-8 into a mammalian expression vector pcDNA3 (Invitrogen) at BglII/BamHI and XhoI. Expression vectors for FLAG-tagged Smad1 and Smad4 were provided by Dr. Rik Derynck (University of California, San Francisco, Calif.). Expression plasmids for constitutively active BMP type IA (ALK3) and IB (ALK6) receptors were provided by Dr. Jeffrey L. Wrana (Hospital for Sick Children, Canada). COS-1 cells were transfected with expression constructs using Tfx-50 according to the manufacturer's instructions (Promega). Cells were lysed 48 h post-transfection, and lysates were immunoprecipitated with anti-HA antiserum (Babco) and immunoblotted with anti-FLAG M2 (Eastman Kodak).

EXAMPLE 5

Electrophoretic Mobility Shift Assay (EMSA)

Figure 3A:
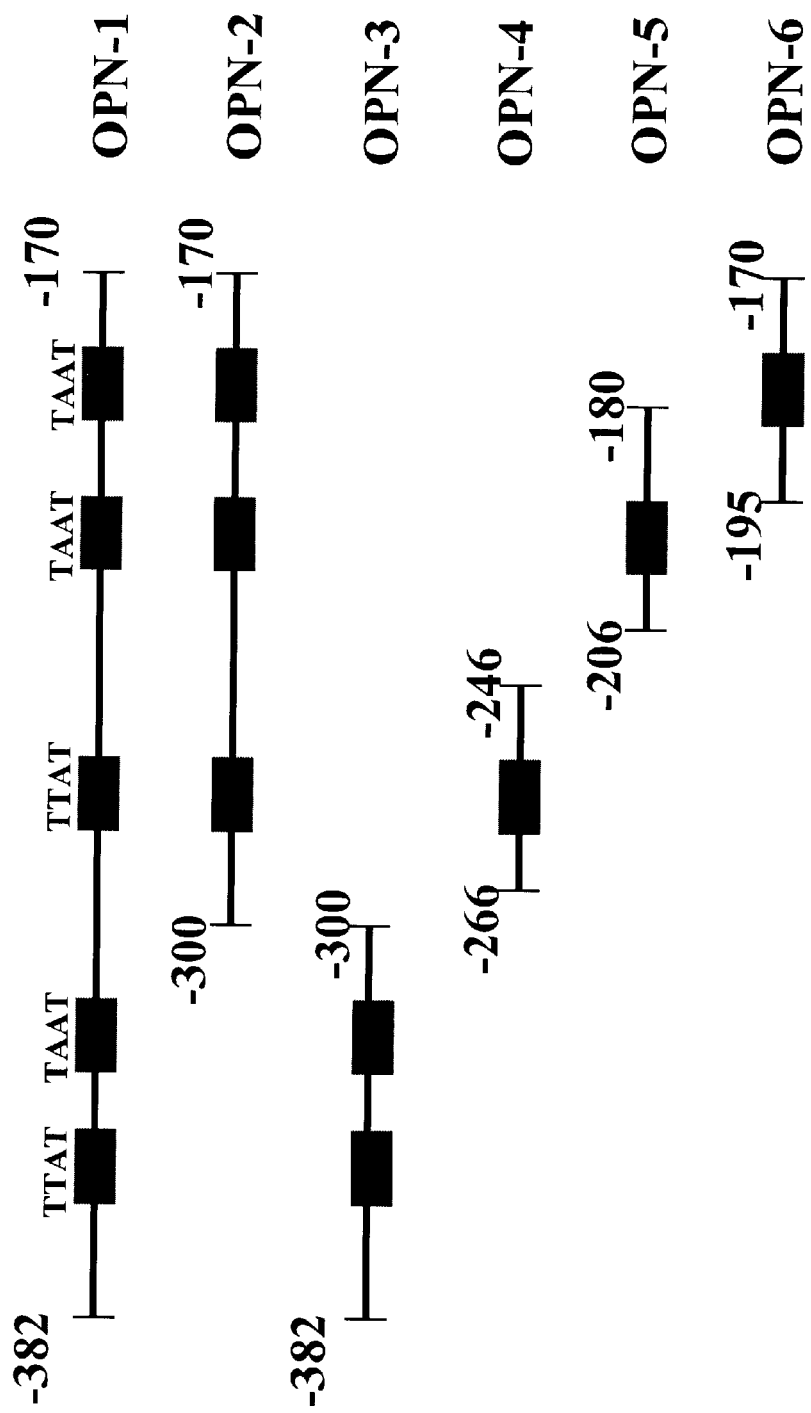
FIGS. 3A–3G show the characterization of a Hoxc-8 DNA binding site from osteopontin promoter.

DNA fragments, OPN1, OPN2 and OPN3, were generated by PCR with primers designed from osteopontin promoter sequence (FIG. 3A). The double-stranded oligomers were created by annealing the following pairs of synthetic oligonucleotides:

5'-AGGGTAATTGGAGGC (SEQ ID No. 1) and 5'-GCCTCCAATTACCCT-3' (SEQ ID No. 2) (Probe S);

5'-CATGACCCCAATTAGTCCTGGCAGCA-3' (SEQ ID No. 3) and 5'-CAGGGATCCATAAGGAAAGG-3' (SEQ ID No. 4) (OPN-4);

5'-GACATCGTTCATCAGTAATGCTTG-3' (SEQ ID No. 5) and 5'-CAAGCATTACTGATGAACGATGTC-3' (SEQ ID No. 6) (OPN-5);

5'-GACATCGTTCATCAGTAATGCTTTG-3' (SEQ ID No. 7) and 5'-CAAAGCATTACTGATGAACCAT GTC-3' (SEQ ID No. 8) (OPN-6).

These DNA fragments or oligomers were radiolabeled by a kinase reaction with $T_4$ kinase and $[\gamma-^{32}P]ATP$. Binding reactions were preincubated for 20 min at 22° C. with indicated proteins in 75 mM NaCl, 1 mM EDTA, 1 mM DTT, 10 mM Tris-HCl (pH 7.5), 6% bovine serum albumin and 25 ng dI/dC in a volume of 19 μl. One μl of DNA probe (0.5 ng, 50,000–100,000 cpm) was added. The reactions were subjected to nondenaturing electrophoresis on a 4% polyacrylamide gel.

EXAMPLE 6

Transfection

The osteopontin promoter from region -266 to -1, relative to the transcription start site, was amplified by PCR from CH10T1/2 cell genomic DNA and cloned into SmaI and XhoI sites of the pGL3-basic vector (Promega) to generate a luciferase reporter construct (OPN-266). Hox-pGL3 reporter bearing the Hoxc-8 binding site (-290 to -166) was constructed using the same strategy but was put into the pGL3-control vector (Promega). The Hox recognition core, TAAT, was replaced with GCCG in Hox-pGL3 by PCR to create mutant Hox-pGL3 (mHox-pGL).

$2\times10^5$ of C3H10T1/2 cells were plated per 60-mm dish and co-transfected the next day by Tfx-50 (Promega) with 0.5 μg of luciferase expression plasmid (pGL3-OPN170) and different expression plasmids as indicated. The pcDNA3-β-gal plasmid was used to balance the amount of the DNA in different groups. pRL-SV40 plasmid was cotransfected for normalization of efficiency. Cells were exposed to the mixture of Tfx-50 and plasmids for 1 hour. The transfected cells were then exposed to 10% DMEM. Forty-eight hours later, the cells were harvested in 1× passive lysis buffer and the lysate was assayed for luciferase activity using Promega's Dual-Luciferase™ Reporter Assay System. Values were normalized using Renilla luciferase activity under the control of the SV40 promoter. The relative value to the control was shown in the figures.

The plasmids encoding various forms of Smad1 fused with a nuclear localization signal (NLS) were constructed by PCR-based strategy into the cytomegalovirus (CMV) promoter-based mammalian expression vector, pCMV5. Each construct contained one of the following regions: Smad1-NL (amino acids 3–276), Smad1-L (aa 145–267), and Smad1-M (101–191). Hoxc-8 was subcloned from pACT2/Hoxc-8 into a mammalian expression vector, pcDNA3 (Invitrogen). C3H10T1/2 cells ($5\times10^4$ cells/well in 12-well culture dishes) were transfected with 0.5 mg of OPN266 luciferase reporter plasmid and different expression plasmids using Tfx-50 as described (Shi and Yang et al., 1999).

EXAMPLE 7

Establishment Of Permanent Cell Lines

The Tet-Regulated Expression System (Gibco) was used to produce Smad1 mutants expressing cell lines in 2T3 osteoblast precursor cells (Harris et al., 1996). A NLS-linked Smad1-NL, Smad1-L, or Smad1-M was subcloned from pCMV5 into pTet-Splice vector (Gibco). Two mg of pTet-splice/Smad1-NL, Smad1-L, Smad1-M, or pTet-splice (control), 2 mg of pTet-tTAk, and 40 ng of pcDNA3 (Clontech) were co-transfected and positive clones were selected by addition of G418 (400 mg/ml) to the growth medium. The expression deletion forms of the Smad1 were determined with Slot-Blot (Bio-Rad) using 5 mg total RNA and [$\alpha$-$^{32}$P]-dCTP labeled probes.

EXAMPLE 8

Bone Marker Gene Expression

Total RNA or mRNA from control and Smad1 expressing cell lines was isolated with STAT-60 (Tel-Test) or with MicroPoly(A)Pure (Ambion) following manufacturers' instructions. Northern blotting was performed using Rapid-Hyb buffer (Amersham) according to the manufacturer's directions. The osteopontin probe was PCR amplified with cDNA from C3H10T1/2 cells as template. The collagen type I(a) and osf-2/cbfa1 probes were kindly provided by Dr. Harris (Univ. of Texas).

EXAMPLE 9

Alkaline Phosphatase And Mineralized Bone Matrix Formation Assay

Bone cell differentiation was determined by alkaline phosphatase assay (Begley et al., 1993) and von Kossa staining (Bharagava et al., 1986).

EXAMPLE 10

Yeast Two-Hybrid Library Screening

To investigate the transcription mechanism in BMP-2/4 induced gene activation, the yeast two-hybrid system was used to identify transcription factors that interact with Smad1 in the BMP-2/4 signaling pathway. An intact Smad1 cDNA fused with the Gal4 DNA binding domain was used as bait plasmid to screen a human U-2 OS osteoblast-like cell library constructed in the pACT2 plasmid vector. Out of 25 positive clones, DNA sequence analysis identified one clone as Hoxc-8 and two clones as Smad4.

Figure 1B:
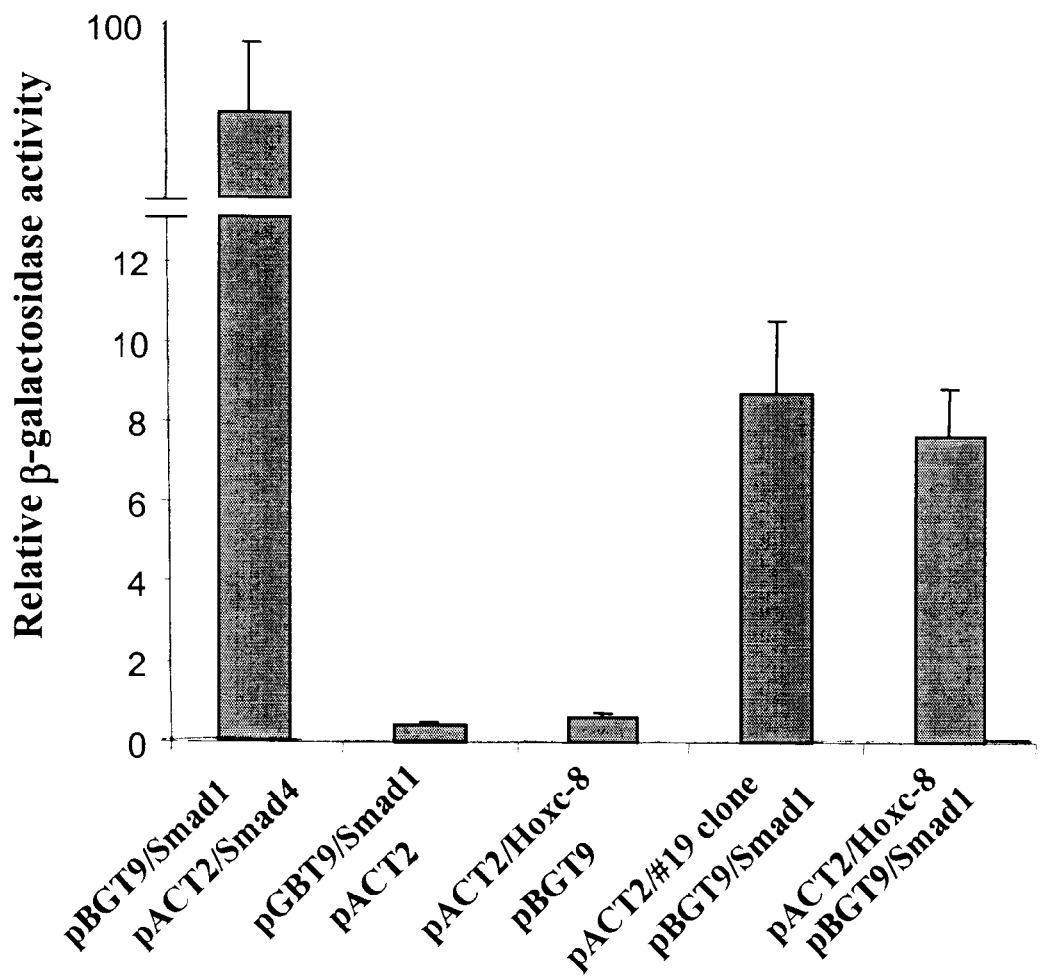

FIG. 1A illustrates the growth properties of the two hybrid system, demonstrating a specific interaction of Smad1 with Hoxc-8 in vivo, which was further confirmed by β-gal liquid assay (FIG. 1B). The yeast bearing both Smad1 and Hoxc-8 plasmids grew on medium deficient in Trp, Leu, and His. When the full length Hoxc-8 fused with the Gal4 DNA binding domain was tested in the two hybrid system, it showed a much stronger interaction with Smad1 (FIG. 1A and B).

EXAMPLE 11

Smad1 Interacts with Hoxc-8 in Vitro and in COS-1 Cells

To further confirm a direct interaction between the two proteins in vitro, glutathione S-transferase (GST) pulldown experiments were also performed with [$^{35}$S] methionine-labeled Hoxc-8 and a GST-Smad1 fusion protein. Hoxc-8 was successfully co-precipitated with the purified GST-Smad1 fusion protein, but not with the GST alone, demonstrating a direct interaction between the two proteins.

Figure 2A:
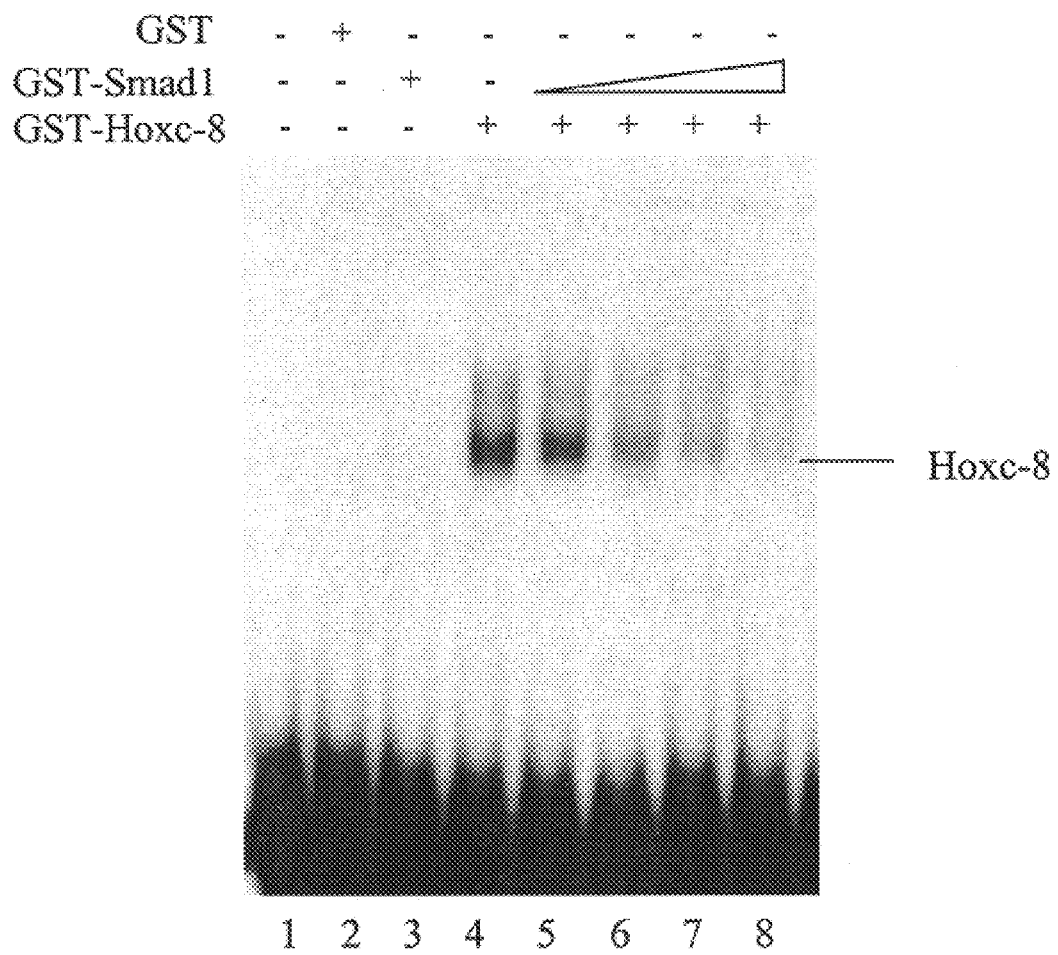
FIG. 2A shows that Smad1 inhibits binding of Hoxc-8 to its DNA binding element in a dose-dependent manner. EMSA was performed using $^{32}$P-labeled Hox binding element alone (lane 1), with GST (lane 2), GST-Smad1(lane 3) or GST-Hoxc-8 protein (lanes 4–8) and different amounts of GST-Smad1(lanes 5–8).

The present invention demonstrates the direct interaction between Smad1 and Hoxc-8 and reveals the Smad1-mediated transcriptional mechanism in BMP-2/4-induced skeleton development. The effect of the interaction on the Hoxc-8 DNA binding activity can be shown by testing the Hoxc-8 protein for its DNA binding property in a gel-shift experiment. The purified GST-Hoxc-8 fusion protein binds to its DNA binding site. The specificity of the binding can be demonstrated with a competition assay. Unlabeled Hoxc-8 DNA binding element eliminated the Hoxc-8 shifted band in a dose-dependent manner, whereas the presence of the Msx-2 DNA binding element (22), another homeodomain-containing protein, did not (data not shown). Significantly, when the purified OST-Smad1 protein was added to the binding reaction, the Hoxc-8 binding band was inhibited in a dose dependent manner (FIG. 2A). Thus, these results indicate that the interaction of Smad1 with Hoxc-8 interferes with the binding of Hoxc-8 to its DNA response element. This appears to mirror the BMP-induced gene activation, since Hoxc-8 has been suggested to be a transcription repressor.

Figure 2B:
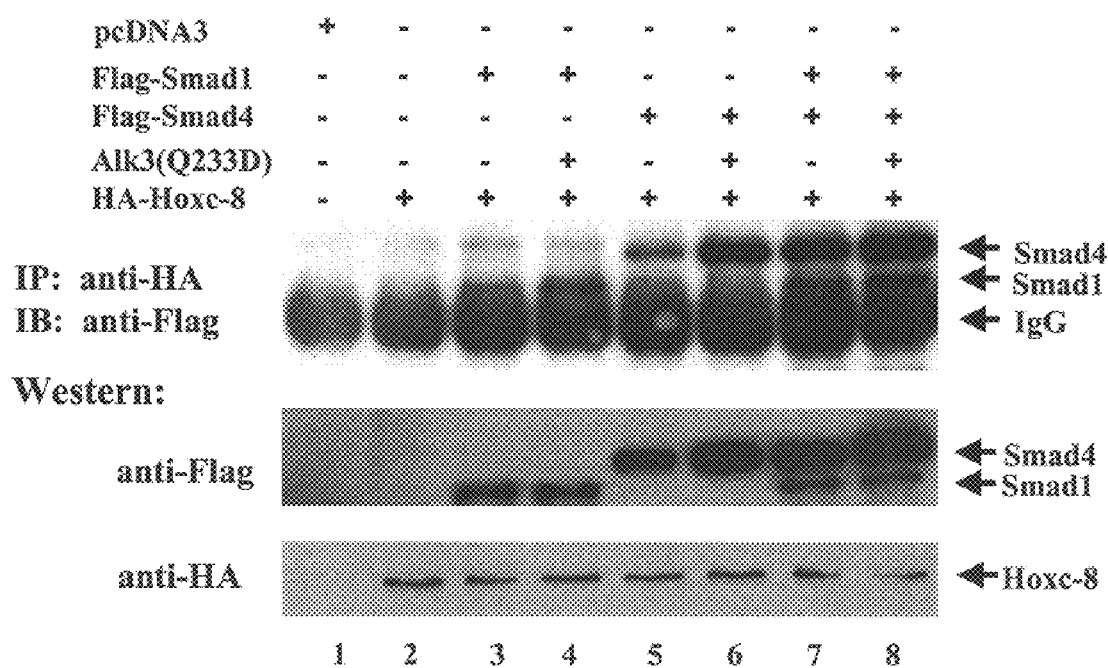
FIG. 2B shows the interaction of both Smad1 and 4 with Hoxc-8 in vivo. FLAG-tagged Smad1 and -4 and HA-tagged Hoxc-8 were co-transfected with or without ALK3 (Q233D). Cell lysates were immunoprecipitated by anti-HA antibody, and the resulting complexes were analyzed by Western blotting with the anti-FLAG antibody. The expression levels of Smad1 and -4 were shown by Western blot with anti-FLAG antibody (middle panel) and of Hoxc-8 with anti-HA antibody (bottom panel).

BMP-2 stimulates phosphorylation of Smad1, and phosphorylated Smad1 in turn binds to Smad4 and takes the complex into the nucleus. It is of interest whether Smad1, Smad4, or the complex of Smad1 and Smad4 also interacts with Hoxc-8 in cells. COS-1 cells were transiently co-transfected with expression plasmids for FLAG-Smad1, FLAG-Smad4, HA-Hoxc-8, and/or constitutively active BMP type IA receptor, ALK3 (Q233D). The cell lysates were immunoprecipitated with anti-HA antibody and immunoblotted with anti-FLAG antibody. FIG. 2B demonstrates that Smad1 (lane 3), Smad4 (lane 5) or both (lane 7) were co-immunoprecipitated with HA-Hoxc-8 in cells. Co-transfection of ALK3 (Q233D) enhanced the interaction of Smad1 (lane 4) or Smad4 (lane 6) with Hoxc-8. However, ALK3 (Q233D) did not significantly enhance the interaction of Smad1 and Smad4 complex with Hoxc-8 (lane 8).

These results show both Smad1 and Smad4 interact with Hoxc-8 in COS-1 cells with or without BMP stimulation, indicating that the phosphorylation of Smad1 is not required for its interaction with Hoxc-8. If this is the case, the BMP-dependent regulation of the interaction is inherent in the intracellular localization of the proteins. Hox proteins are homeodomain transcription factors localized in the nucleus, whereas both Smad1 and Smad4 are cytoplasmic. It is likely that the interaction occurs only when Smad1 or the complex translocates to the nucleus upon its phosphorylation induced by BMP receptors.

EXAMPLE 12
Osteopontin Promoter Contains a Hoxc-8 Binding Element

Figure 3B:
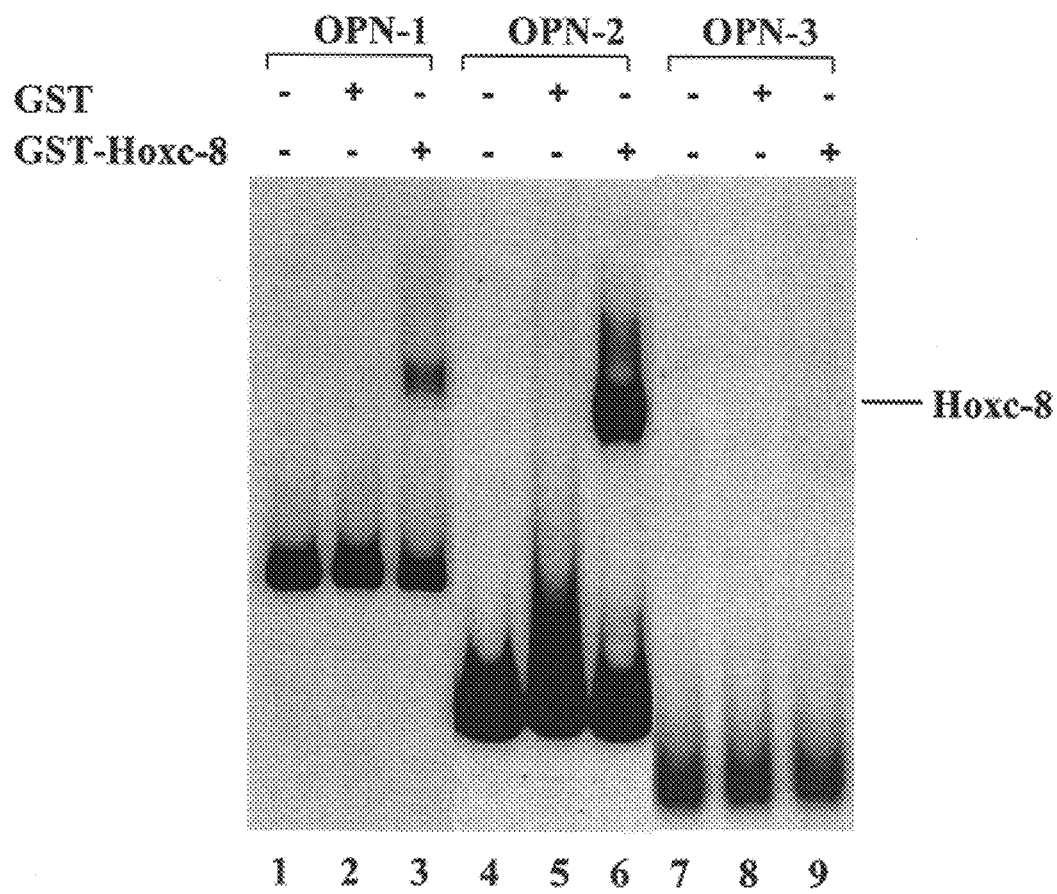
Figure 3C:
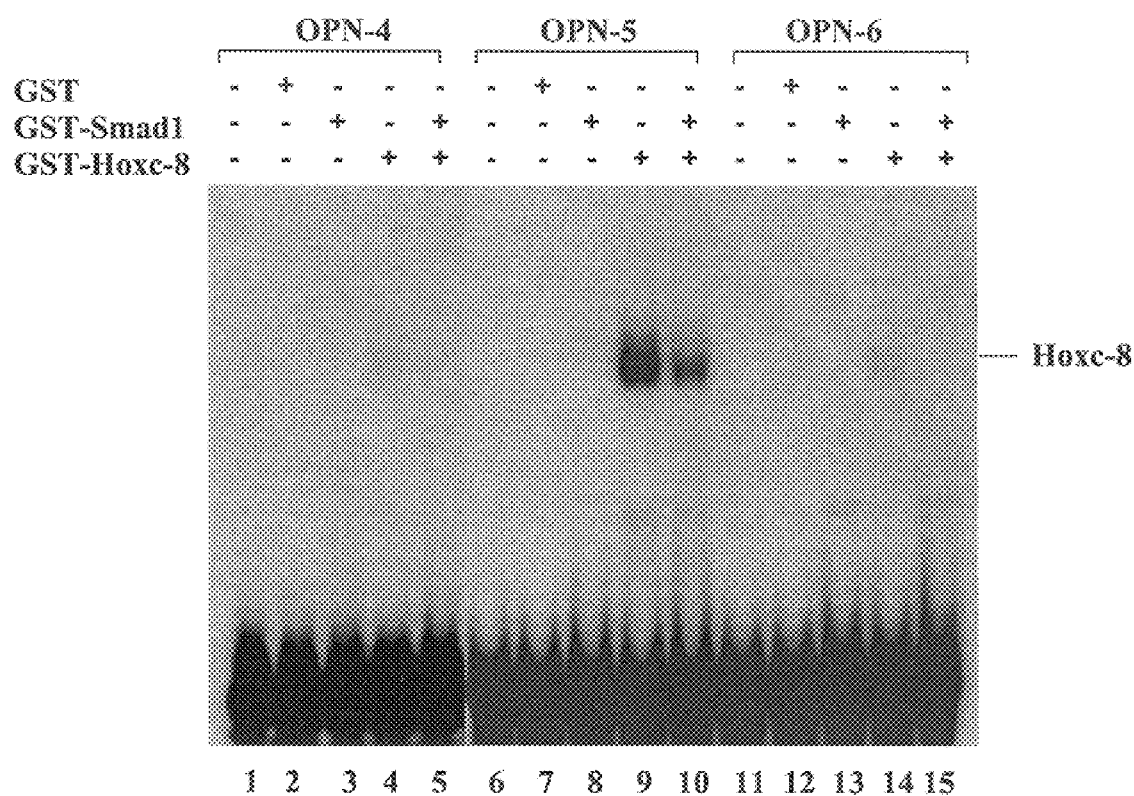

In order to investigate whether the interaction between Smad1 and Hoxc-8 binds DNA and modulates transcriptional activity, the BMP-2 inducible genes were examined. Through a comparison of promoter sequences, putative Hox binding sites were found in four BMP-2 responsive bone matrix protein genes, bone sialoprotein, osteopontin, osteonectin and osteocalcin, which have served as marker genes for osteoblast differentiation. The osteopontin promoter was examined, since its mRNA expression was rapidly activated in response to BMP-2 treatment in C3H10T1/2 mesenchymal cells. There are five putative Hox binding sites, with a core sequence of Ta/tAT, within the first 382 bp of the 5' flanking region in osteopontin gene (FIG. 3A). When the 212 bp DNA fragment from -382 to -170 (OPN-1) containing all five putative Hox sites was used for gel shift assay in incubation with purified GST-Hoxc-8 protein, one Hoxc-8 binding band was observed, indicating that there is only one Hoxc-8 binding site in the osteopontin promoter (FIG. 3B). Subsequent gel shift assays with shorter probes (OPN-2 and OPN-3) localized the Hoxc-8 binding element in the region from -206 to -180 (encompassed by OPN-2) (FIG. 3A and C). When three single putative Hox binding probes (OPN-4, -5 and -6) were used, Hoxc-8 only bound to OPN-5, located at -206 to -280. Neither GST alone nor GST-Smad1 fusion protein could bind to any of the probes used in this series of gel shift assays. When the TAAT core sequence of Hoxc-8 binding site in OPN-5 was mutated to GCCG (mOPN-5), Hoxc-8 binding was abolished.

Figure 3D:
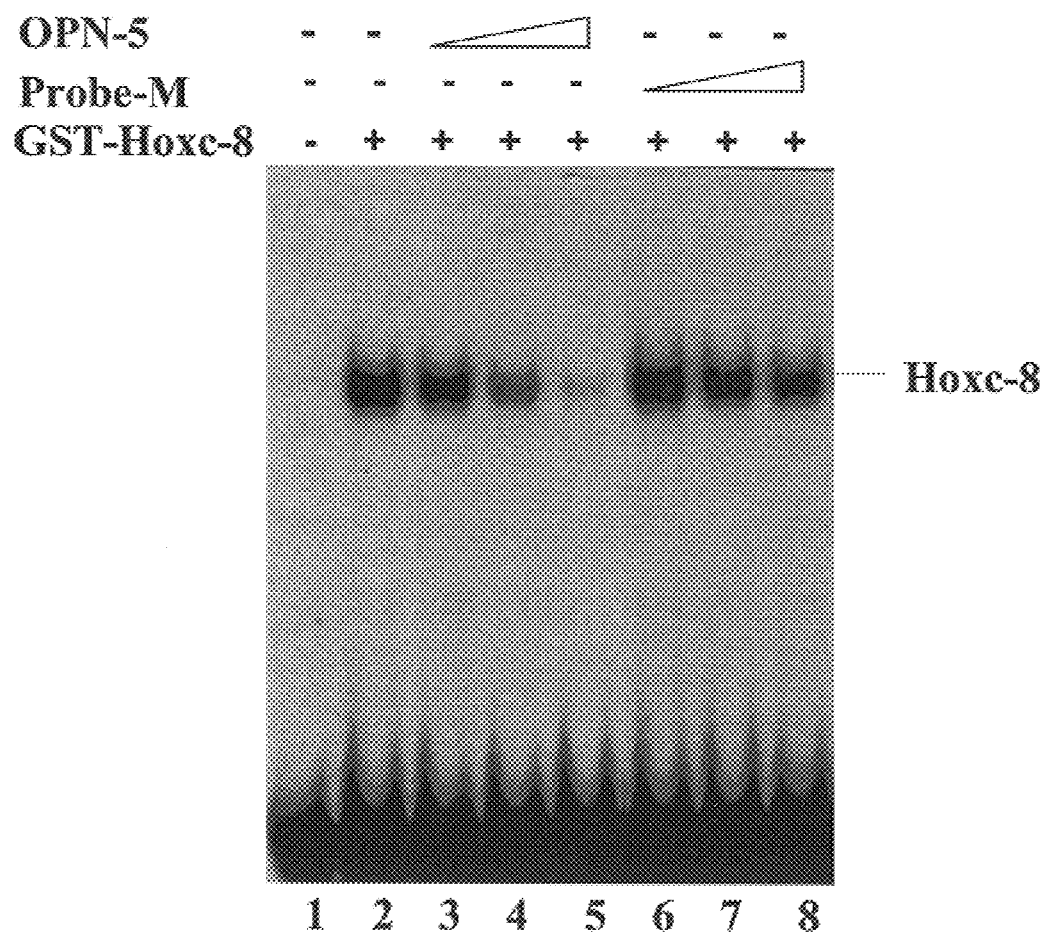

The specificity of the Hoxc-8 binding to the DNA was determined by a gel shift competition assay (FIG. 3D). Unlabeled Hoxc-8 DNA binding element inhibited the shifted band in a concentration dependent manner in which a 100-fold excess of the specific cold probe eliminated the Hoxc-8 binding, whereas a 100-fold excess of the Msx-2 DNA binding element did not. Msx-2 is a homeodomain-containing protein, but it does not belong to the Hox family. The Msx-2 DNA binding element was identified from the osteocalcin promoter, and its flanking regions of the core sequence is different from Hoxc-8 binding site.

There are three TAAT and two TTAT putative Hox sites identified for the osteopontin promoter. Hoxc-8 binds to only one of the TAAT core sequences (-206 to -180), suggesting that the flanking regions are also important for Hoxc-8 binding. The Hoxc-8 binding site, including its flanking regions, is highly conserved in chicken, mouse, pig and human. The other four putative Hox sites may be involved in other homeodomain protein binding or may not be authentic Hox binding sites.

EXAMPLE 13
Smad1 Inhibits Binding of Hox Proteins to DNA

Figure 3E:
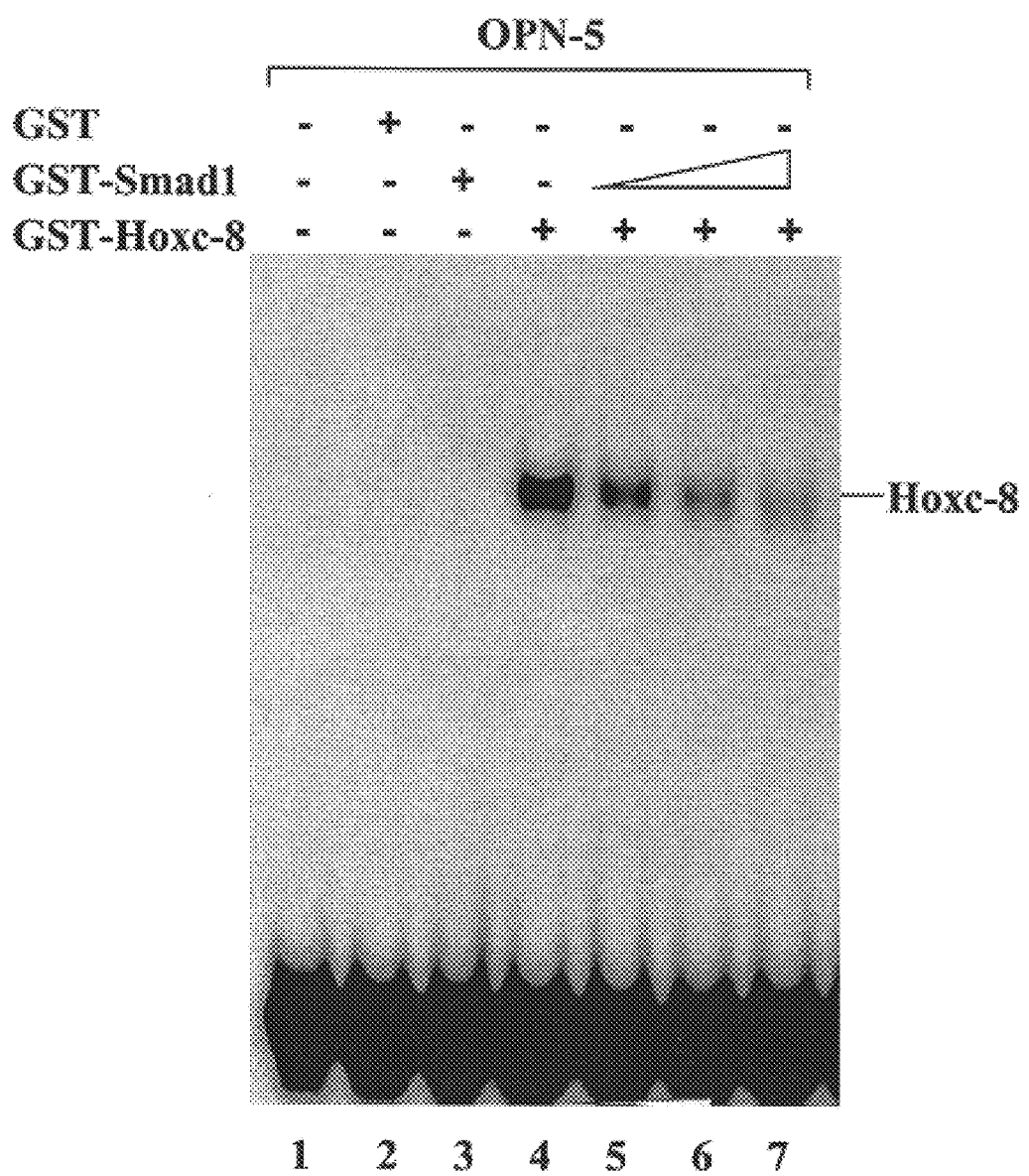

Purified GST-Smad1 was examined for the effect of its interaction with Hoxc-8 on Hoxc-8 DNA binding activity. When GST-Hoxc-8 protein and its DNA binding element (OPN-5) were incubated with increasing amounts of GST-Smad1 protein, the binding of Hoxc-8 to the DNA probe was inhibited in a concentration-dependent manner (FIG. 3E). The same amount of GST-protein did not have an effect on Hoxc-8 binding activity. These results suggest that the interaction of Smad1 with Hoxc-8 dislodges Hoxc-8 from its response element.

Because the signalling networks of the TGF-β superfamily are very complex, it is important to understand the specificity of the interaction between Hox and Smad proteins. Hoxa-9 was chosen as a well characterized homeobox DNA binding protein to examine its interaction with different Smad proteins. Two other homeodomain proteins, Msx-1 and Msx-2, were also used for gel shift assays for the same purpose. Msx-1 and Msx-2, found at different loci than the Hox gene clusters, are involved in development of teeth. The expression of both genes is coordinately regulated by BMP-2 and BMP-4.

Figure 3F:
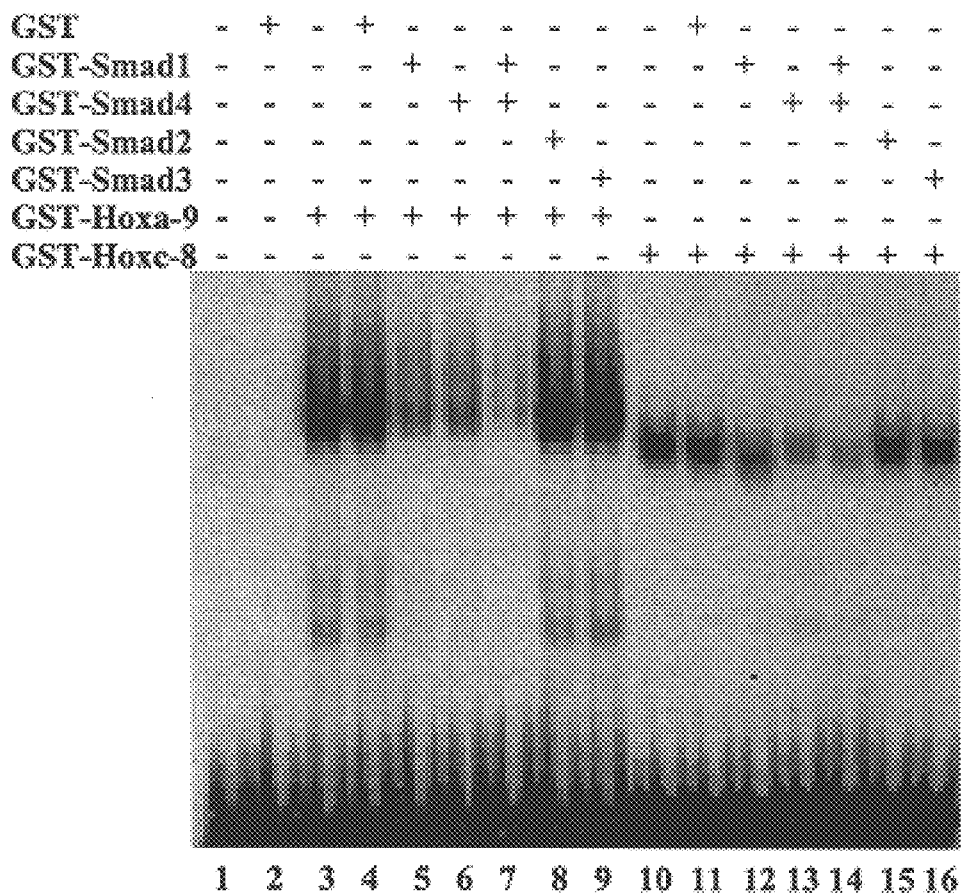
Figure 3G:
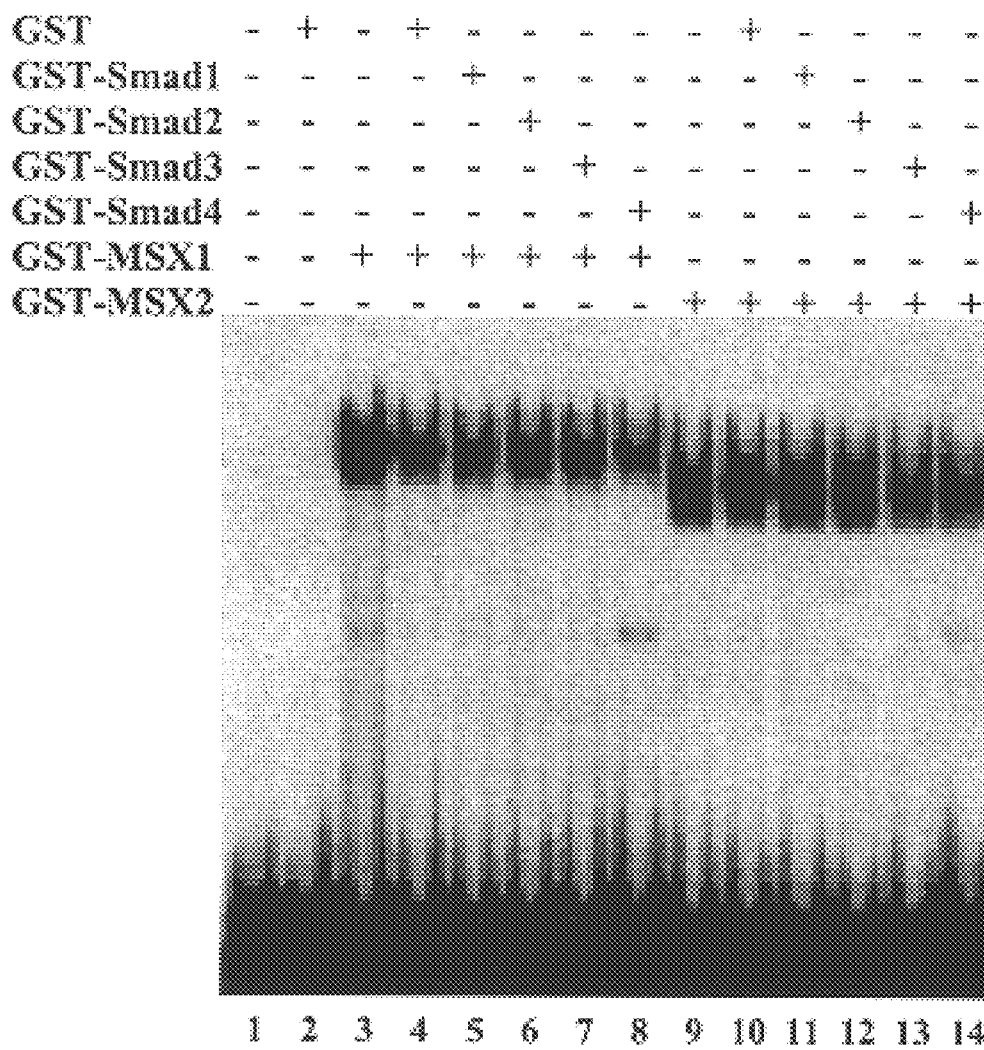

To estimate the relative strength of the interactions between the Smads and homeodomain proteins, the same amounts of Hoxc-8 and Hoxa-9 or Msx-1 and Msx-2 proteins were used in each of the gel shift assays with a fixed amount of different Smad proteins. Smad1 and Smad4 inhibited both Hoxc-8 and Hoxa-9 binding, and the inhibition was enhanced when both Smad proteins were added together (FIG. 3F). In contrast, neither Smad2 nor Smad3 interacted with these two Hox proteins. Neither of the Msx proteins interacted with any of the four Smad proteins (FIG. 3G). GST did not affect Hox or Msx protein binding. The homeodomain, a well conserved DNA binding motif, is the region highly conserved between Hoxc-8 and Hoxa-9, suggesting that Smad1 interacts with other Hox proteins involved in BMP signalling.

EXAMPLE 14
Hox Binding Site Mediates BMP-Induced Transcription

Figure 4A:
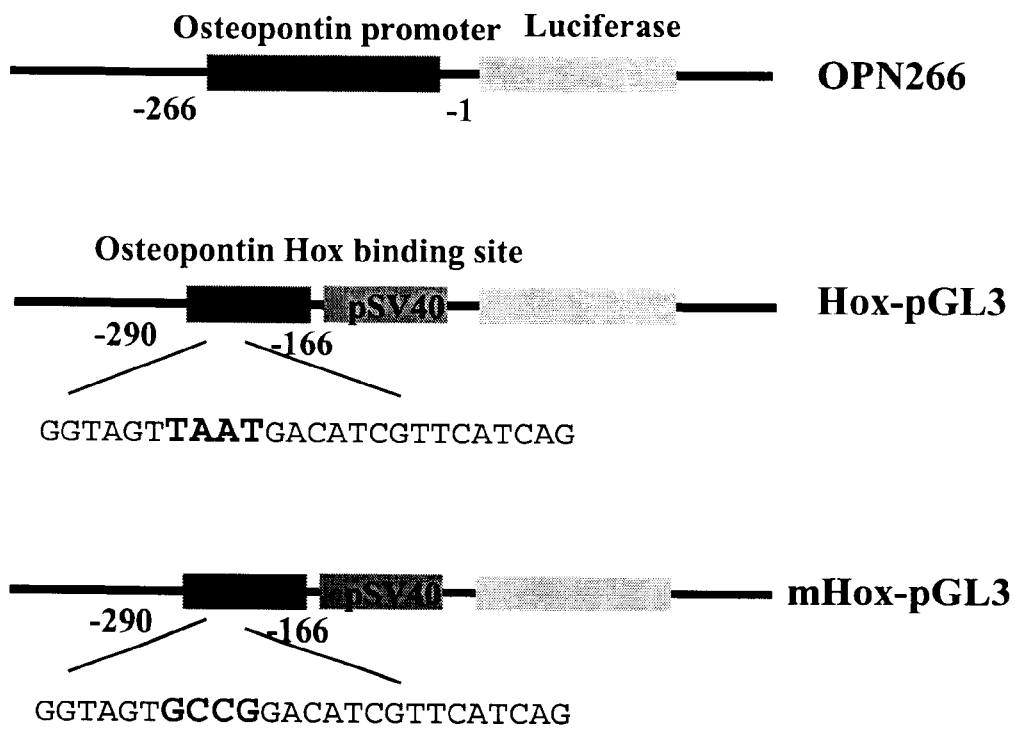
FIGS. 4A–4D show that BMP-2-induced osteopontin gene transcription is mediated by a Hoxc-8 binding site.
Figure 4B:
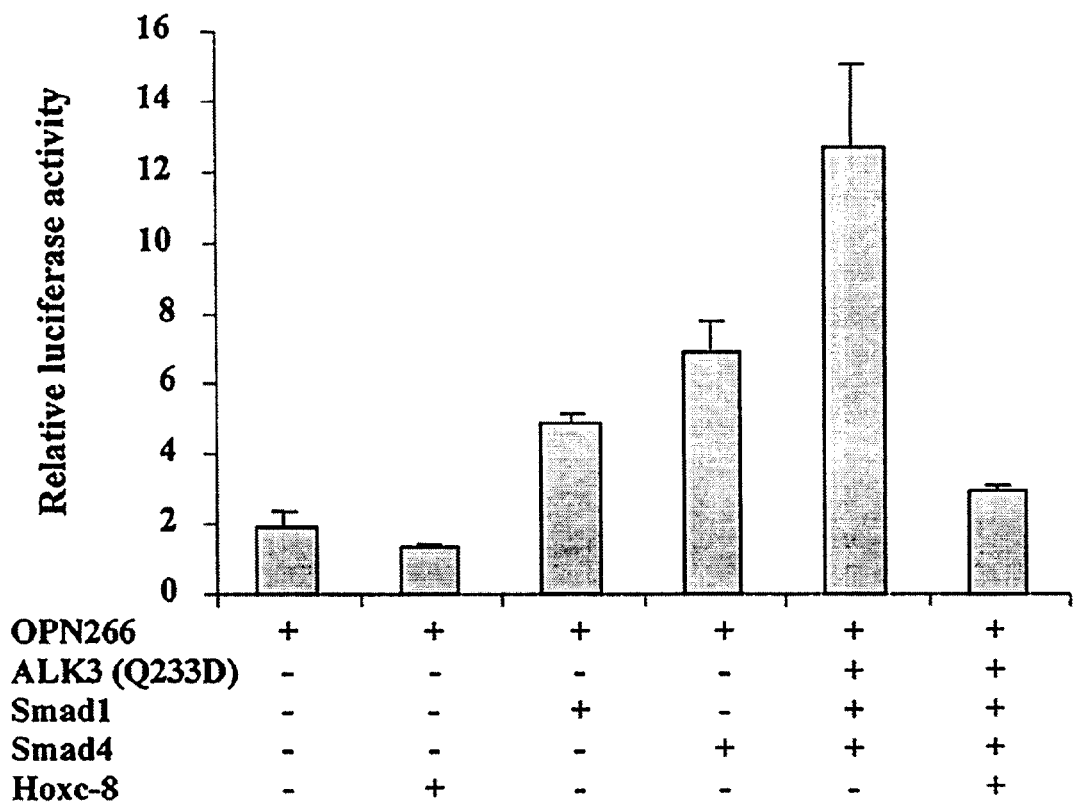

To examine whether Hoxc-8 binding site functions as BMP-2/4 response element, a 266 bp osteopontin promoter fragment containing the Hoxc-8 binding site was cloned into the pGL3-basic luciferase reporter vector to generate OPN-266 reporter plasmid (FIG. 4A). Transfection of the OPN-266 construct in C3H10T1/2 mesenchymal cells showed that the reporter activity was stimulated moderately when Smad1 or Smad4 expression plasmids were co-transfected (FIG. 4B). The luciferase activity was significantly enhanced when the OPN-266 reporter construct was co-transfected with ALK3 (Q233D), Smad1, and Smad4 expression plasmids. Furthermore, the ALK3 (Q233D)-induced transcriptional activity was completely abolished when Hoxc-8 was overexpressed (FIG. 4B).

Figure 4C:
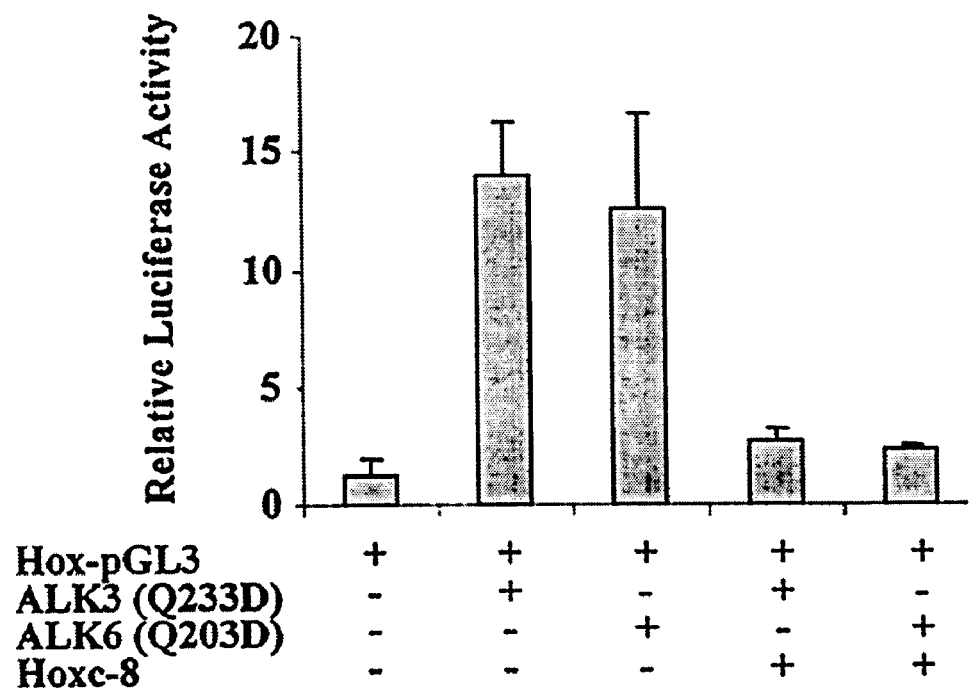

To further define the transcription activity of the Hoxc-8 binding site, a shorter osteopontin promoter fragment containing the Hoxc-8 binding site was linked to a luciferase reporter vector under the control of the SV40 promoter (Hox-pGL3) or the tk minimal promoter (Hox-tk). Luciferase reporter activities were induced more than 13- and 11-fold in C3H10T1/2 mesenchymal cells co-transfected with ALK3 (Q233D) or ALK6 (Q203D) respectively (FIG. 4C). Most importantly, overexpression of Hoxc-8 suppressed the ALK3 (Q233D)-induced or ALK6 (Q203D)-induced reporter activity. These results demonstrate that the Hox binding site mediates BMP signalling and that Hoxc-8 functions as a transcriptional repressor. Most interestingly, the level of luciferase reporter activity was induced 20-fold when the Hox-tk construct was co-transfected into C3H10T1/2 mesenchymal cells with Smad1, Smad4 and constitutively active type IB BMP receptor expression plasmids (ALK6), indicating Hoxc-8 binding site acts as a BMP-2/4 response element. Co-transfection of Smad1 or Smad4 expression plasmids alone or with ALK6 did induce reporter activity significantly (FIG. 4B). The results suggested that Smad4 is required to form hetero-oligomers with the phosphorylated Smad1 for translocation into the nucleus, and BMP-2/4 activates gene transcription by removing the repressor, Hoxc-8, through the interaction of Smad1 with the Hoxc-8 protein. It becomes likely that BMP-2/4 stimulates mesenchymal cell differentiation into osteoblasts by removing transcriptional repression by Hoxc-8.

Figure 4D:
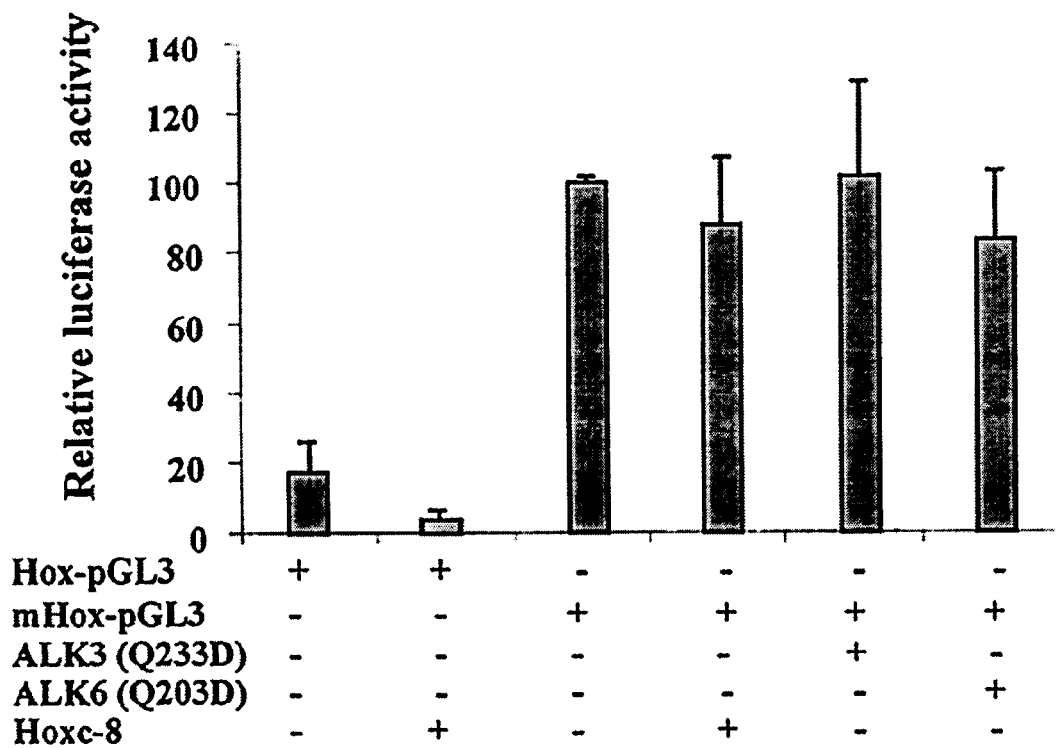

To validate whether the Hoxc-8 site mediates BMP signalling, the core nucleotides of the Hoxc-8 binding site were mutated from TAAT to GCCG to create mHox-pGL3. Transfection of the mutant construct completely abolished the ALK3 (Q233D)-induced or ALK6 (Q203D)-induced reporter activity and eliminated Hoxc-8 inhibition in C3H10T1/2 cells (FIG. 4D). These results confirm that the osteopontin Hox binding site is a BMP response element.

EXAMPLE 15
Two Regions within the MH1 and Linker of Smad1 Contribute to the Interaction with Hoxc-8

Figure 5A:
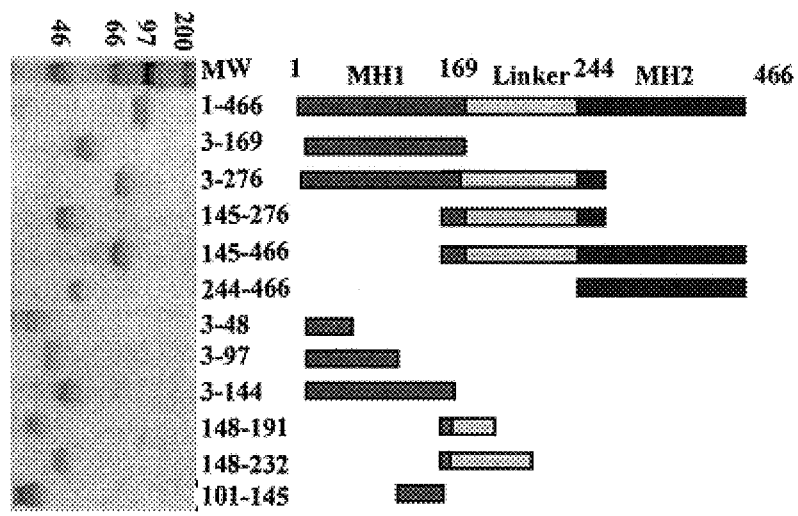
FIG. 5A–5C show that the N-terminal domains of Smad1 interact with Hoxc-8.

A direct interaction has been detected between Smad1 and Hoxc-8 in yeast by two hybrid studies, in mammalian cells by co-immunoprecipitation, and in vitro by pull down assays. In order to determine region(s) mediating the protein-protein interaction, a series of Smad1 deletions was constructed encoding either the conserved N-terminal domain, MH1, with (3–276) or without (1–169) the linker (145–276), or the conserved C-terminal domain, MH2, with (145–466) or without (244–466) the linker (FIG. 5A). The association of these proteins was tested in yeast two-hybrid assays. The wild type Smad1 and its deletion mutants, as well as the empty bait were individually transformed into yeast cells containing a Hoxc-8 prey plasmid and β-gal activity was determined. The wild type and mutants carrying MH1 and/or the linker domains interacted with Hoxc-8, and showed a significantly increased β-gal activity compared with the negative control, whereas the MH2 domain alone (276–466) did not interact with Hoxc-8 (data not shown).

Figure 5B:
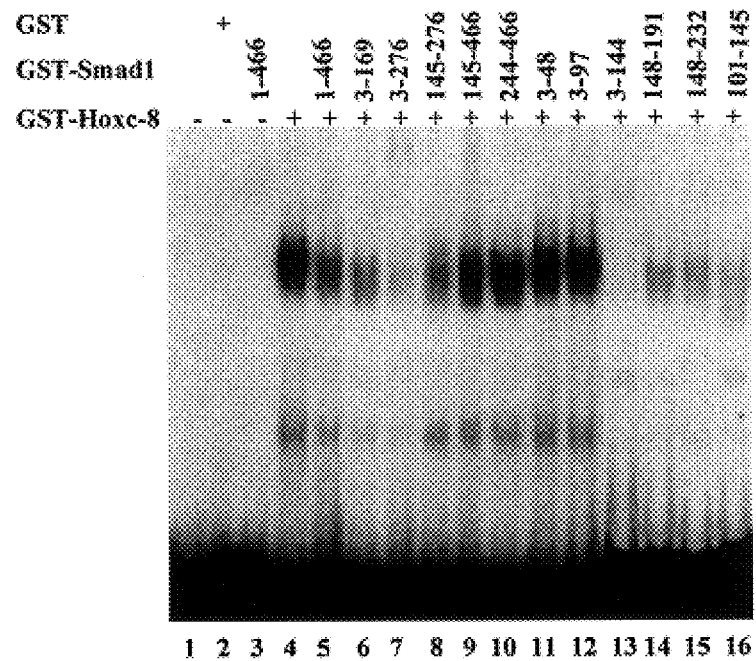
Figure 5C:
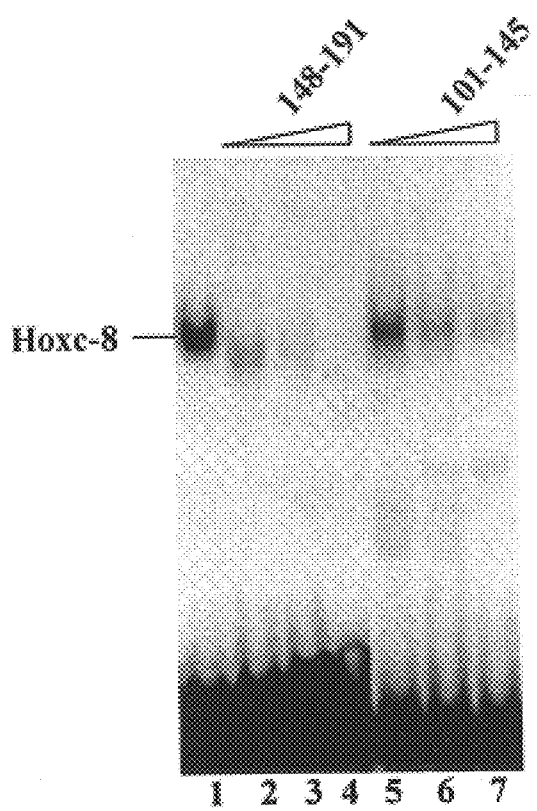

Previously, it was shown that Hoxc-8 binds to a 23-bp element derived from the osteopontin promoter. Gel shift assays showed that the GST-Smad1 fusion protein inhibited Hoxc-8 binding to this element in a dose-dependent manner (Shi and Yang, 1999). A nest of Smad1 fragments fused with GST were expressed in bacteria as shown in FIG. 5A. Equal amounts of purified GST-Smad1 wildtype and truncated mutants were analyzed in a gel shift assay for mapping the domain(s) that inhibit the Hoxc-8 DNA binding activity. As shown in FIG. 5B, the binding of Hoxc-8 (lane 4) was reduced by the addition of wild type Smad1 (lane 5) and mutant Smad1 containing MH1 only (lane 6) or MH1 plus linker (lane 7). A strong inhibition was observed in the Smad1 retaining both MH1 and linker domain (lane 7). In contrast, the binding of Hoxc-8 remained unchanged when GST-MH2 was added (lane 10). Note that the inhibitory effect of the linker region on the Hoxc-8 binding to the DNA probe was masked in the presence of MH2 (lanes 8 and 9). Further gel shift assays using smaller deletions resolved two regions (148–191 and 101–145), within the Smad1 MH1 domain and MH1-linker junction regions that interact with Hoxc-8 (FIG. 5B, lanes 14 and 16). Both fragments inhibited Hoxc-8 binding in a dose-dependent manner (FIG. 5C). These results indicate that two regions within the N-terminal of Smad1 are accountable for the inhibition of Hoxc-8 binding to its cognate DNA element.

EXAMPLE 16
A Homeodomain is Responsible for the Hoxc-8 Association with Smad1

Hox proteins have a similar homeodomain (HD) in common, consisting of a highly conserved DNA binding motif of 60 amino acids (Sharley, et al., 1995). Besides the homeotic domain that lies from amino acids (aa) 149 to 209, Hoxc-8 contains two other conserved peptide regions: an octapeptide (aa 1–8) and a hexapeptide (aa 137–142 SEQ ID NO:11) (Le Mouellic et al, 1988). The hexapeptide of Leu-Met-Phe-Pro-Trp-Met SEQ ID NO:11 lies upstream from the homeodomain and is presumably involved in the interaction with Hox-assisting cofactors (Phelan et al, 1995 and Sharley et al., 1997). A recent study has revealed a direct contact between the pentapeptide of Hoxb-1 and its DNA binding partner, the Pbxl protein (Piper, et al., 1999).

Figure 6A:
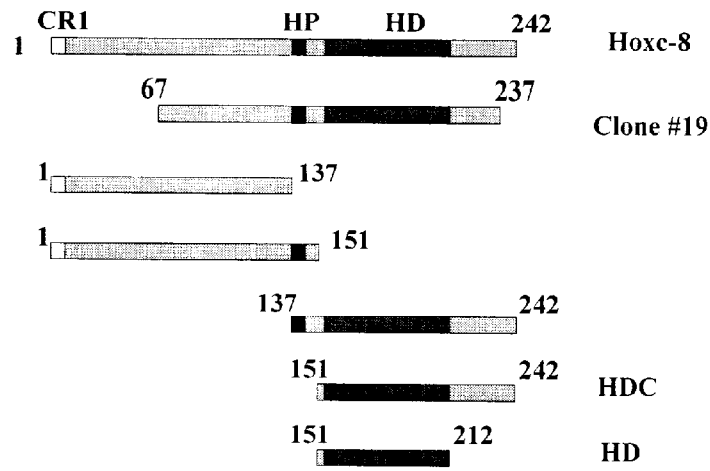
FIG. 6A–6D show that the homeodomain of Hoxc-8 interacts with Smad1.
Figure 6B:
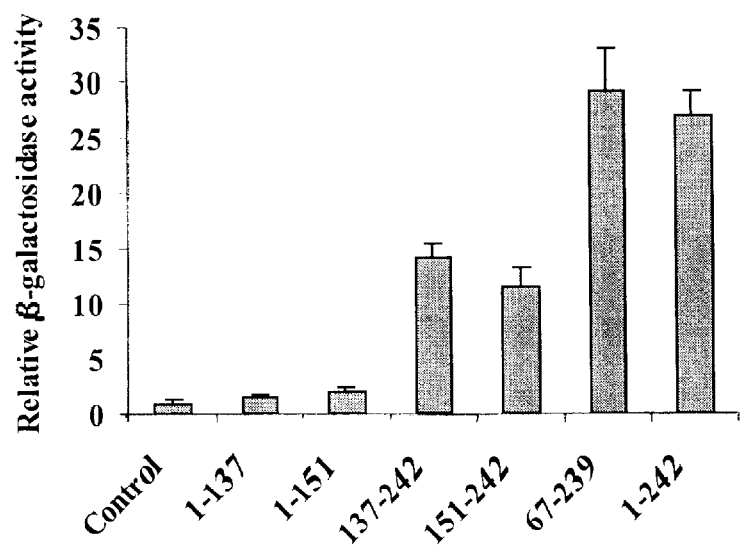

Deletion analysis was also done with the Hoxc-8 prey to determine the region critical for the association with Smad1. An empty prey, the full-length form, as well as deletion mutants of Hoxc-8 were separately transformed into yeast cells harboring a Smad1 bait plasmid and β-gal activity was subsequently assayed. FIG. 6B shows that the full length Hoxc-8 (1–242) and its homeodomain-containing deletions (137–242, 151–242, and 68–237) interacted with Smad1 with higher β-gal activity when compared with the negative control. The association was stronger with full-length Hoxc-8 and the original clone containing amino acid residues 68–237 (Shi and Yang, 1999), indicating that regions outside HD are involved in the interaction. Deletion of the homeodomain ablated the interaction, suggesting that homeodomain may be directly involved in the Hoxc-8-Smad1 interaction.

Figure 6C:
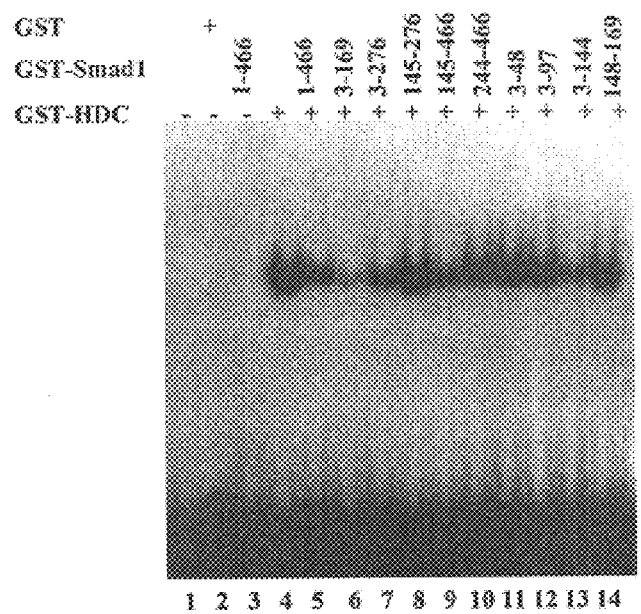
Figure 6D:
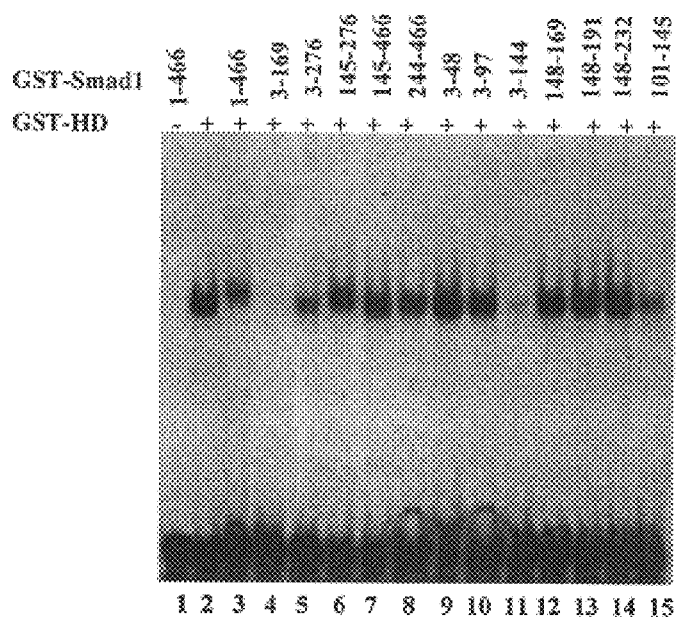

To confirm that the homeodomain (HD) is the region that interacts with Smad1, deletions encoding homeodomain (149–209) or homeodomain and its C-terminal flanking sequence (HDC, 151–242, FIG. 6) were cloned into a bacterial expression vector to make mutants of the Hoxc-8 fusion proteins. HD-containing deletion mutants of Hoxc-8 (FIGS. 6B–D) were tested for their binding to DNA in the presence of either wildtype or mutant Smad1. As shown in FIG. 6D, purified GST-HD and GST-HDC bound to the DNA probe (lanes 4 and 9, respectively). The binding was inhibited by the wildtype Smad1 (lanes 5 and 10) and the mutant containing the MH1 and linker region (lanes 6 and 11), which showed the strongest inhibition on the Hoxc-8 binding (FIG. 6C, lane 7). Similar to the gel shift assays with wildtype Hoxc-8, the binding of HDC was also inhibited by smaller deletions encoding portions of the MH1 or linker (lanes 7 and 8) of Smad1. Interestingly, the binding of homeodomain was only inhibited by a mutant encoding amino acid residues 101–145 (lane 12), but not by 148–191 (lane 13), suggesting that more than one protein-protein contact may be involved in the Smad1-Hoxc-8 interaction.

Figure 7A:
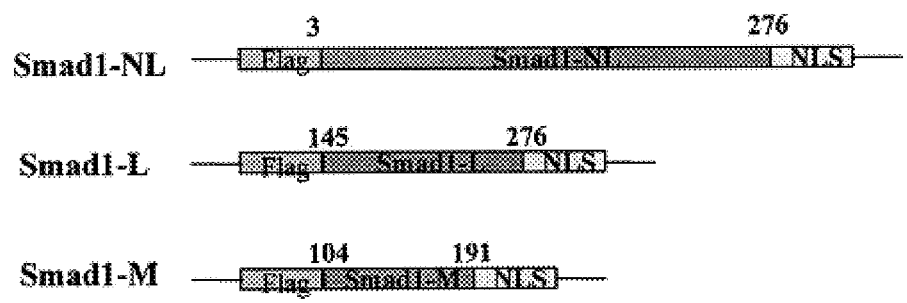
FIG. 7A–7D show the Smad1 domains containing Hoxc-8 interaction regions induce bone cell differentiation.

EXAMPLE 17
Two Domains of Smad1 Interacting with Hoxc-8 Induce Osteopontin Promoter Activation Previously, it has been reported that Hoxc-8 binds to a 266 bp osteopontin promoter fragment and represses reporter gene transcription (Shi and Yang et al., 1999). Co-transfection of Smad1, Smad4, and a constitutively active form of the BMP type I receptor ALK3 (Q233D) in C3H10T1/2 mesenchymal cells induces reporter gene transcription. To investigate the transcription activity of the Hoxc-8 interaction domains of Smad1, three cDNA fragments containing either one or two Hoxc-8 interaction domains fused with a nuclear localization signal (NLS) were cloned into a CMV5B mammalian expression vector (FIG. 7A). Co-transfection was performed with 1 5 expression plasmids for Smad1 containing amino acids 3–276 (Smad1-NL), 145–276 (Smad1-L), or 104–191 (Samdl-M) and OPN-266, the recombinant reporter construct containing Hoxc-8 binding site (Shi and Yang et al., 1999). The osteopontin promoter activity was stimulated 3–5 fold by all three Smad1 fragments containing either one or both Hoxc-8 interaction domains. These data suggest that the Hoxc-8 interaction domains of Smad1 mimic the BMP signaling and are sufficient to induce gene transcription.

EXAMPLE 18
Hoxc-8 Interaction Domains of Smad1 Induce Bone Cell Formation

Figure 7B:
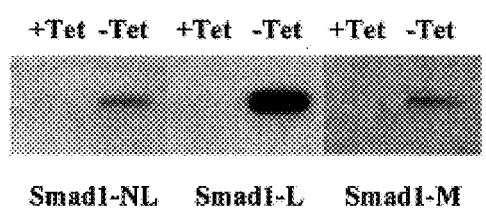

To examine whether the interaction between Smad1 and Hoxc-8 stimulates osteoblast differentiation, Smad1-NL, Smad1-L and Smad1-M were also cloned into a tetracycline-regulated expression system. These plasmids and a control vector were permanently transfected into 2T3 cells, a well characterized osteoblast precursor cell line (Ghosh-Choudhury et al., 1996 and Chen, et al., 1998). Five to ten tetracycline-regulated positive clones were selected by slot blotting and Northern hybridization using corresponding cDNA probes. FIG. 7B demonstrates that in three of the clones, expression of the Smad1 fragments was regulated by tetracycline.

Figure 7C:
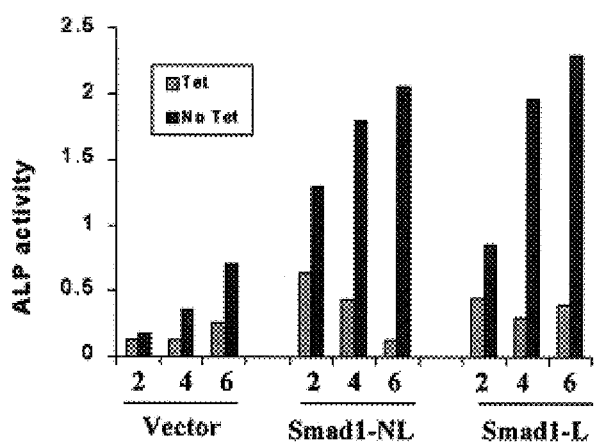
Figure 7D:
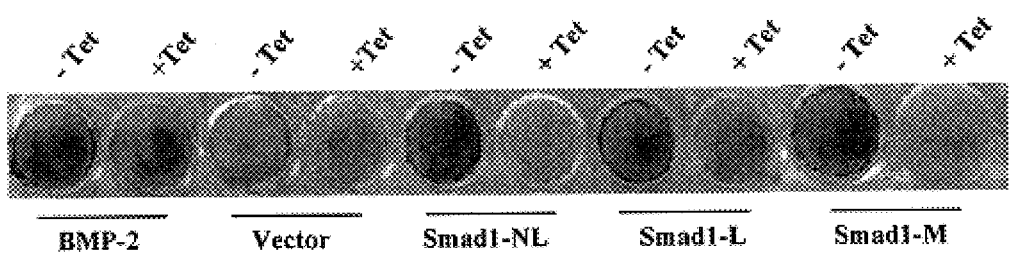

Alkaline phosphatase activity is a hallmark in bone formation, and induction of its activity in progenitor cells marks the entry of a cell into the osteoblastic lineage. Stable expression of Smad1-NL, Smad1-L or Smad1-M by withdrawal of tetracycline effectively stimulates alkaline phosphatase activity in a time-dependent manner, whereas alkaline phosphatase activity remained unchanged in control cells permanently transfected with pTet-Splice vector (FIG. 7C). Most importantly, stable expression of those Smad1 fragments in 2T3 cells induced bone mineralization (FIG. 7D). These results indicate that the interaction between Smad1 and Hoxc-8 initiates the entire program for osteoblast differentiation.

SUMMARY

Figure 8:
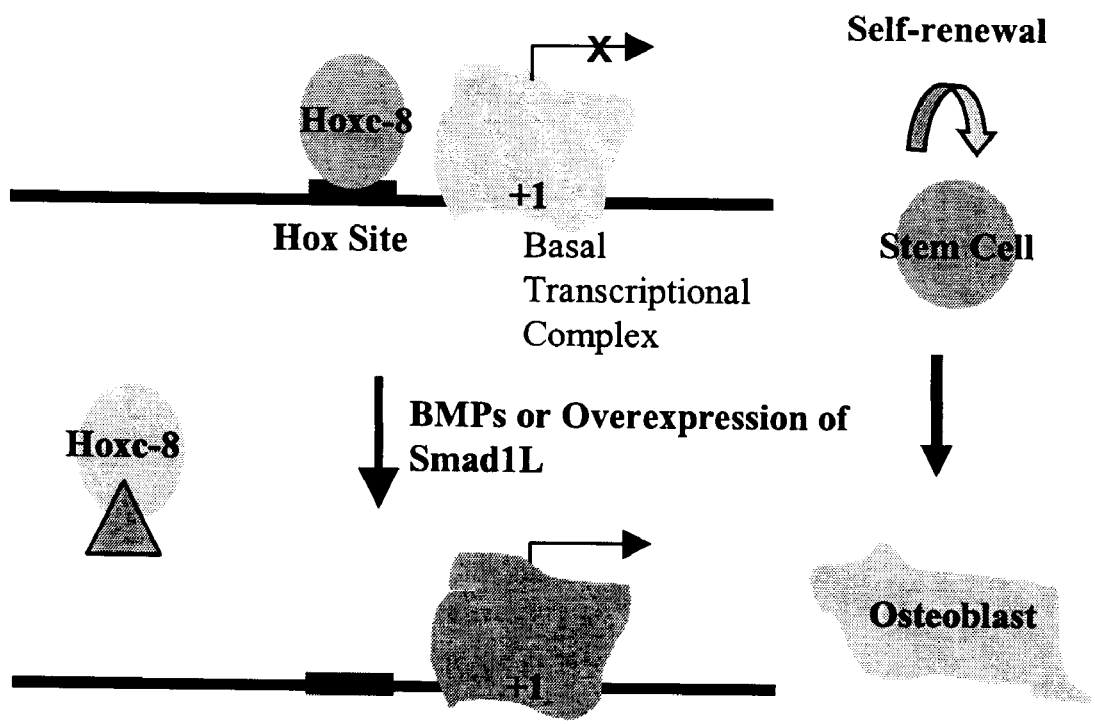
FIG. 8 shows a proposed model for the mechanism of Hoxc-8 interaction domains of Smad1 mimicking BMP signaling and inducing bone cell differentiation. Hoxc-8 represses gene transcription in the basal state in the pluripotent and self-renewable stem cells. When the Smad1-Hoxc-8 interaction domains are expressed, they enter the nucleus and bind to Hoxc-8. The interaction of Smad1 fragments with Hoxc-8 inhibits Hoxc-8 binding to its cognate DNA element in the bone marker genes (such as osteopontin) which then derepresses Hoxc-8 and activates gene transcription and subsequently induces the formation of osteoblast cells.

The protein domain of Hoxc-8 interacting with Smad1 has been mapped using a yeast two-hybrid system and a gel shift assay. The Hoxc-8 homeodomain, a well conserved DNA binding motif, interacts with Smad1. These results suggests that Smad1 may inhibit binding of most Hox and homeodomain proteins to their DNA binding sites. BMP-2/4 may either turn on or off gene transcription depending on the spatial and temporal expression of these Hox and homeodomain proteins as well as the promoter context (FIG. 8D), since Hox and homeodomain proteins function as both activators and repressors. This sophisticated regulation mechanism may explain why there has been no BMP-2/4 DNA response element characterized. Thus, BMP-2/4 may stimulate mesenchymal cell differentiation by regulating binding of Hox or homeodomain proteins from their DNA binding sites. The present invention demonstrates that BMPs induce the interaction between Smad1 and Hoxc-8 protein, stimulating osteoblast differentiation in precursor cells. These observations reveal the function and relationship between BMPs and Hox genes during embryonic skeleton development.

The following references were cited herein:
1. Wang et al., Proc. Natl. Acad. Sci. 85, 9484–9488 (1988).
2. Francis, P. H., et al., Development 120, 209–218 (1994).
3. Mead, P. E., et al., Nature 382, 357–360 (1997).
4. Ahrens, M., et al., DNA & Cell Biol. 12, 871–880 (1993).
5. Heldin, C., et al., Nature 390, 465–471 (1997).
6. Hoodless, P. A., et al., Cell 85, 489–500 (1997).
7. Nishimura, R., et al., J. Biol. Chem. 273, 1872–1879 (1998).
8. Sharkey, M., et al., TIG 13, 145–151 (1997).
9. Maconochie, et al., Annu. Rev. Genet. 30, 529–556 (1996).
10. Charite, J., et al., Cell 78, 589–601 (1994).
11. Lu, H. C., et al., Development 124, 1643–1651 (1997).
12. Simeone, et al., Proc. Natl. Acad. Sci. 84, 4914–4918 (1987).
13. Hardy, A., et al., Development 121, 4329–4337 (1995).
14. Lagna, G., et al., Nature 383, 832–836 (1996).
15. Liu, F., et al., J. Nature 381, 620–623 (1996).
16. Hata, A., et al., Nature 388, 82–87 (1997).
17. Chen, X., et al., Nature 383, 691–696 (1996).
18. Hunt, & Krumlauf Annu. Rev. Cell Biol. 8, 227–256 (1992).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inducing the expression of genes that contain Hox protein binding elements and encode bone matrix proteins in vitro, comprising the step of:

transfecting an expression plasmid encoding Smad1 into a cell, wherein said expressed Smad1 interacts with Hox protein and inhibits the binding of said Hox protein to DNA, thereby inducing the expression of genes that contain Hox protein binding elements.

2. A method of inducing the expression of a gene encoding osteopontin, comprising the step of:

transfecting expression plasmid encoding Smad1 into a cell, wherein said expressed Smad1 interacts with Hoxc-8 protein and inhibits the binding of said Hoxc-8 protein to DNA, thereby inducing the expression of said gene encoding osteopontin.

3. A method of screening for a compound that stimulates bone formation, comprising the steps of:

contacting a cell with a compound; and determining the ability of said compound to inhibit binding of Hoxc-8 to a gene, wherein inhibition of binding results in induction of said gene, thus indicating that the compound stimulates bone formation.

4. The method of claim 3, wherein said compound is selected from the group consisting of an antibody or fragment thereof, synthetic drugs, synthetic proteins and a phosphorylated form of Smad1 or fragments thereof.

5. The method of claim 3, wherein determination of inhibition of binding of Hoxc-8 to a gene is by a method selected from the group consisting of a gel-shift assay, transcription assay, Northern blotting, and Western blotting.

6. The method of claim 3, wherein said gene is selected from the group consisting of osteopontin, sialoprotein, osteonectin, and osteocalcin.

* * * * *